United States Patent [19]

Bailey, Sr. et al.

[11] Patent Number: 5,658,324

[45] Date of Patent: Aug. 19, 1997

[54] SYSTEM AND METHOD FOR THE REDUCTION OF SECONDARY TRAUMA

[75] Inventors: Richard F. Bailey, Sr., Pennington, N.J.; Ronald A. Fisher, New York, N.Y.

[73] Assignee: Promdx Technology Inc., New York, N.Y.

[21] Appl. No.: 227,634

[22] Filed: Apr. 14, 1994

[51] Int. Cl.$^6$ .................................................. A61F 7/02
[52] U.S. Cl. ............................ 607/104; 607/112; 607/114
[58] Field of Search ................................. 607/96, 104–7, 607/114, 112

[56] References Cited

U.S. PATENT DOCUMENTS

| | | | |
|---|---|---|---|
| 3,995,621 | 12/1976 | Fletcher et al. | 607/104 X |
| 4,026,299 | 5/1977 | Sauder | 607/104 |
| 4,072,152 | 2/1978 | Linehan | 607/104 X |
| 4,098,279 | 7/1978 | Golden | 607/104 |
| 4,738,119 | 4/1988 | Zafred | 607/104 |
| 5,433,083 | 7/1995 | Kuramarohit | 607/104 X |
| 5,449,379 | 9/1995 | Hadtke | 607/107 |

*Primary Examiner*—Angela D. Sykes
*Attorney, Agent, or Firm*—Steven M. Hoffberg; Furgang & Milde LLP

[57] ABSTRACT

An apparatus and method for providing cryotherapy and controlled compression using a non-chlorofluorocarbon pressurized refrigerant supplied in a disposable canister, including a canister adapter, an inject valve which mates to the adapter, providing a steady flow rate of refrigerant to provide a predetermined cooling and a selectively initiated rapid flow of refrigerant to rapidly establish operating conditions, a conduit for connecting the inject valve and a maze fluid flow path in which the heat of vaporization of the refrigerant fluid cools an object in proximity to the maze, a bladder for accumulating vaporized refrigerant outside the maze and an exhaust valve having a predetermined relief pressure, venting refrigerant gas from the bladder to the atmosphere, thereby inflating the bladder with gaseous refrigerant to a specified pressure.

22 Claims, 10 Drawing Sheets

SYSTEM AND METHOD FOR THE REDUCTION OF SECONDARY TRAUMA

FIELD OF THE INVENTION

The present invention relates to the field of reusable, pressurized, cold-therapeutic devices which employ canisters of pressurized refrigerant and are used in the treatment of secondary trauma. More particularly, the invention relates to a system which provides, in portable form, the benefits of application of cold and pressure for pre-exercise and post-exercise muscular conditioning, the immediate treatment of musculo-skeletal injuries and inflammatory conditions, therapeutic reduction of tissue metabolism and the reduction of chemotherapeutically-induced hair loss.

BACKGROUND OF THE INVENTION

"Cryotherapy" is defined as the treatment of injury using the benefits derived by application of both cold and pressure. Such therapy has been shown to be particularly effective in treating musculoskeletal trauma resulting from a severe blow or by the application of a wrenching force to the body, e.g. lacerations, sprains, strains and fractures. This type of injury may be accompanied by a tearing of tendons, ligaments or other tissue, and starts the body's own natural healing process. See Sloan et al., "Effects of Cold and Compression on Edema", *The Physician and Sports Medicine*, 16(8) (1988); Bailey, "Cryotherapy", *Emergency*, 40–43 (August, 1984); Cryomed Brochures.

In order to minimize secondary trauma subsequent to a primary musculoskeletal insult, prompt treatment is required. This treatment should immobilize the trauma site, ease pain and minimize the risk of secondary tissue damage which usually accompanies breaks, sprains and strains.

An injury will almost immediately produce pain and will be followed rapidly by an accumulation of blood, interstitial fluids and lymphatic fluids. In addition, injured cells will release histamine and other substances which act to perpetuate the inflammation process and increase the permeability of the vasculature. For a number of reasons, a free radical process ensues. The inflammatory process also causes the release of chemicals and causes conditions under which damaged collagen dissolves. The extent of this collagen damage depends on a number of factors, including the extent of the inflammatory process.

The collagen removal process forms a part of the normal healing process, and under certain circumstances, is desirable in that it allows reconstruction of the tissue by collagen regrowth. Unfortunately, in most circumstances, the damaged collagen is replaced by a random regrowth, forming a scar. While scar formation may be necessary to replace the lost tissue matrix, in many circumstances the scar impairs a return to normal functioning. Thus, scar formation in a joint, where uninjured collagen is linearly dispersed, tends to proceed after the injury by randomly-fashioned replacement, which may interfere with joint mobility and produce chronic pain.

The body's healing response is natural and necessary for restoring the functioning of the damaged tissue and the body as a whole. This natural process may produce detrimental side effects that, if not properly controlled, can exacerbate patient discomfort, impede recovery and result in long term or permanent impairment of the injured area.

Damage to the tissue may allow the formed blood components to leave the vasculature in the area of the injury (called a "hematoma"). Enhanced permeability of the blood vessels may lead to an accumulation of fluids in the extracellular space (called "edema"). This fluid causes swelling, which may form part of a self-perpetuating process of inflammation. Further, in circumstances when the pressure in the tissue exceeds the perfusion pressure in the capillary microcirculation, the flow of oxygenated blood in that tissue becomes insufficient and the tissue becomes hypoxic, eventually leading to hypoxic necrosis. This process, called a "compartment syndrome", may occur when an external pressure is applied to tissues which exceeds the perfusion pressure, or when an inflammatory process in the tissue causes the buildup of interstitial fluid with an increase in pressure.

Secondary trauma is a process by which a primary injury causes inflammation, edema and/or hematoma, which secondarily is responsible for further tissue damage. If the secondary process is treated, slowed or its course modified, the extent of this secondary injury may be reduced. Thus, after a musculoskeletal injury, edema and/or hematoma may result, causing tissue compression and other effects. This compression can result in further injury while the swelling lasts, and prevent other treatments from being effectively applied. Under normal circumstances, secondary trauma lasts approximately one to three days after a primary musculoskeletal insult, and during this period, further treatment, including surgery, may have to be postponed.

It is known that the immediate application of compression and cold will slow down tissue metabolism and response to injury so that a slower and more controlled process may ensue. Thus, the art teaches the use of ice pack compresses. Additionally, U.S. Pat. No. 3,871,381 to Roslonski teaches the introduction of a pressurized volatile refrigerant through a controlled flow rate valve, which cools a maze-passage in a flexible device. A pressure relief valve maintains a back-pressure in the system.

Besides injuries, there are other applications for cryotherapy. For example, normal tissues, such as hair follicles, may be spared the effects of cancer chemotherapy by the topical application of pressure and cold around the time of chemotherapeutic treatments. See, e.g., Dean, J. C. et al., "Prevention of Doxorubicin-induced Scalp Hair Loss," *New England Journal of Medicine*, Dec. 27, 1979, 301(26) :1427–29; H. F. P. Hillen, et al., "Scalp cooling by cold air for the prevention of chemotherapy-induced alopecia," *Netherlands Journal of Medicine*, 37 (1990) 231–235; Cline, B. W., "Prevention of chemotherapy-induced alopecia: a review of the literature," *Cancer Nursing*, 1984, 7:221–228; Dean, J. C., et al. "Scalp hypothermia: A comparison of ice packs and the Kold Kap in the prevention of doxorubicin-induced alopecia," *J. Clin. Oncol.*, 1983, 1:33–37; Bulow J., et al., "Frontal subcutaneous blood flow, and epi- and subcutaneous temperatures during scalp cooling in normal man," *Scand. J. Clin. Lab Invest.*, 1985, 45:505–508; Parbhoo, SP, et al., "An improved technique of scalp hypothermia to prevent adriamycin/mitozantrone induced alopecia in patients with advanced breast cancer," *Clinical Oncology and Cancer Nursing*, Stockholm, 1985, 232 (abstract); Gregory, R. P., et al., "Prevention of doxorubicin-induced alopecia by scalp hypothermia: relation to degree of cooling," *Br. Med. J.*, 1982, 284:1674. Chemotherapeutic agents which cause alopecia which may be reduced by cryotherapy include anthracycline antibiotics, e.g. doxorubicin or epirubicin, nucleoside analogs, e.g. 5-fluorouracil, folate antagonists, e.g. methotrexate and alkylating agent, e.g. cyclophosphamide.

In addition, cryotherapy may also be employed for other medical purposes, where control of metabolic rate is desired.

For example, U.S. Pat. No. 3,821,381 to Roslonski relates to a system for applying pressure and cold to an injury, using chlorofluorocarbons as a refrigerant fluid. It is also known to circulate a cooled fluid through a conduit in a bandage. Cold and pressure are therefore known treatments for traumatic injuries, as well as inflammatory pathologic processes which involve externally accessible organs.

Additionally, the device disclosed in Roslonski, U.S. Pat. No. 3,871,381 relates to a system for applying cold and pressure to an injury using a fluorocarbon refrigerant. This system, however, presents a number of drawbacks. First, the design of Roslonski's flow path allows refrigerant liquid to pool in some areas, while other areas do not receive liquid, thus causing uneven tissue cooling. Further, a crimp in one portion of the device may block a flow of coolant liquid to other portions of the device, likewise causing uneven cooling and additionally causing noise.

The temperature of these known systems depend in large part on the composition of the refrigerant fluid employed, which has a boiling plateau slightly above the freezing point of water. These systems therefore allow the maintenance of the device at a slightly higher temperature. These known systems also have an operating temperature which depends in lesser part on the rate at which heat is removed by the refrigerant, which in turn depends on the rate of volatization of the refrigerant. Other performance factors include the ambient temperature, body temperature, atmospheric pressure, pressure within the device, refrigerant composition and flow rate of the refrigerant.

Chlorofluorocarbon refrigerants are known to be available and to be used alone or in mixtures. Some mixtures have a boiling characteristic with a plurality of plateaus. Known refrigerants like Freon 11, Freon 12 and Freon 114 have boiling points of approximately 75 F. (24 C.), −22 F. (−30 C.) and 39 F. (3.8 C.) respectively, and these may be mixed to form a refrigerant solution having approximately the same boiling plateaus. See Freon Product Information, Du Pont (1973). In practice, the lowest boiling component of such a refrigerant mixture acts to propel the refrigerant from the canister and precool the remaining refrigerant liquid as it enters the maze. The mid temperature boiling refrigerant acts to cool the tissue by boiling in the maze at a temperature approximately the same as the desired tissue temperature. Lastly, the highest boiling component acts as a heat transfer agent to improve the effectiveness of the device, since it vaporizes before it reaches the bladder. Thus, the lowest temperature in the heat transfer portion of the cryotherapy device, using the known refrigerants, will be around 36–39 F., thereby posing a small risk of tissue freezing, unless too much refrigerant mixture is injected so that the lowest boiling component is present in substantial quantities. These mixtures, therefore, may be used in open-loop cryotherapy systems, with minimal or imprecise flow regulation, and with low risk of tissue freezing.

Known second generation mid-boiling refrigerants, including 124 and 142B, have much lower boiling points than the corresponding mid-boiling CFC components, e.g. 12.2 F. and 14.4 F. respectively and therefore pose a substantial risk of tissue freezing when substantial quantities of refrigerant liquid (at about atmospheric pressure) vaporize in proximity to the skin. Conventional CFC-based systems need not carefully control the flow of refrigerant, because the major penalty of too high a flow rate is the premature exhaustion of the CFC supply and a high flow rate of gas (and/or liquid in extreme cases) exhausted from the system.

The following patents relate to known refrigerant systems: Lodes, U.S. Pat. No. 2,529,092; Benning, U.S. Pat. No. 2,641,579; Ashkenaz, U.S. Pat. No. 2,987,438; Munro, U.S. Pat. No. 3,733,273; Borchardt, U.S. Pat. No. 3,812,040; Hutchinson, U.S. Pat. No. 3,940,342; Murphy, U.S. Pat. No. 4,055,054; Orfeo, U.S. Pat. No. 4,533,536; Nikolsky, U.S. Pat. No. 4,495,776; Ermack, U.S. Pat. No. 4,510,064; and Nikolsky, U.S. Pat. No. 4,603,002.

Brown, U.S. Pat. No. 2,694,395 relates to a pneumatic pressure garment for application of therapeutic pressure. Gottfried, U.S. Pat. No. 3,153,413 relates to a pressurized bandage with splint functions. Towle, et al., U.S. Pat. No. 3,171,410 relates to a pneumatic wound dressing. Gardner, U.S. Pat. No. 3,186,404 relates to a pressure device for therapeutic treatment of body extremities. Romano, U.S. Pat. No. 4,135,503 relates to an orthopedic device having a pressurized bladder for spinal treatment. Curlee, U.S. Pat. No. 4,622,957 relates to a therapeutic corset for applying pressure to a portion of the back. Cronin, U.S. Pat. No. 4,706,658 relates to a gloved splint, providing a shock absorbing treatment and possible heat removal from the hand.

Robbins et al., U.S. Pat. No. 4,175,297 relates to an inflatable pillow support having automated cycling inflation and deflation of various portions thereof.

Artemenko et al., U.S. Pat. No. 3,683,902 relates to a medical splint apparatus, having an inflatable splint body and a circulated cooling agent, cooled by solid carbonic acid $CO_2$. Davis et al., U.S. Pat. No. 3,548,819 relates to a pressurized splint adapted to apply a thermal treatment to a human extremity. Nicholson, U.S. Pat. No. 3,561,435 relates to an inflatable splint having a coolant chamber to apply pressure and cool to a human extremity. Berndt et al., U.S. Pat. No. 3,628,537 relates to a self-retaining cold wrap which treats an injury with cold and pressure. Baron, U.S. Pat. Nos. 4,300,542 and 4,393,867 relate to a self-inflating compression device for use as a splint.

Golden, U.S. Pat. No. 4,108,146 relates to a cooling thermal pack with circulating fluid which conforms to body surfaces to apply a cooling treatment. Moore et al., U.S. Pat. No. 4,114,620 and Gammons et al., U.S. Pat. No. 4,149,541 relate to treatment pads with circulating fluid for providing a hot or cold treatment to a patient. Brannigan et al., U.S. Pat. No. 4,575,097 relates to a thermally capacitive compress for applying hot or cold treatments to the body.

Arkans, U.S. Pat. No. 4,331,133 relates to a pressure measurement apparatus for measuring the pressure applied by a pressure cuff to a human extremity.

Kiser et al., U.S. Pat. No. 4,502,470 relates to a device for assisting in pumping tissue fluids from a foot and ankle up the leg.

Stark, U.S. Pat. No. 3,000,190 relates to an apparatus providing body refrigeration, for use in high ambient temperature environments by workers.

FR 2,133,680 relates to a system for cooling objects, including beverage cans, using fluorocarbons, e.g. Freon.

Nelson, U.S. Pat. No. 2,051,100, Burkhardt, U.S. Pat. No. 2,463,516 and Richards, U.S. Pat. No. 4,103,704 relate to pressure relief valves.

Ninomiya et al., U.S. Pat. No. 4,286,622 relates to a check valve assembly.

Martin et al., U.S. Pat. No. 2,550,840, Both et al., U.S. Pat. No. 2,757,964, Galeazzi et al., U.S. pat. No. 2,835,534, Mura, U.S. Pat. No. 3,314,587, White, U.S. Pat. No. 3,976,110 and Turner, U.S. Pat. No. 4,281,775 relate to pressurized container dispensing valves and systems containing same. Frost, U.S. Pat. No. 3,273,610 relates to a pressurized container valve and detachable dispensing attachment device.

Known aerosol-type cans have a stem which protrudes upwardly, and which is depressed to release the contents of the can. The nozzle is generally secured to the stem by friction. A cap is generally provided to prevent inadvertent release of the contents of the can. Known refrigerant-supply cans are generally sealed and release their contents only after a metal diaphragm is punctured. Thus, Vos, U.S. Pat. No. 3,756,472 relates to a system for use with a pressurized canister to produce a desired stream characteristic during ejection of the pressurized contents. This system may be mounted atop an aerosol container.

Portability, a desired characteristic, requires a system which has good long term storage capability, ease of replacement of any expendable components, and light weight self-contained design, without need for an external power source and relatively safe design.

SUMMARY AND OBJECTS OF THE INVENTION

The present invention relates to a self contained, portable secondary trauma reduction system that simultaneously surrounds sprains, strains, twists, pulls and painful sites with deep-penetrating, controlled, therapeutic cold having the additional characteristic of consistent controlled pressure. The system according to the present invention includes a reusable, pressurized, cold therapeutic device employing canisters of pressurized refrigerant for the treatment of secondary trauma.

The present invention includes a number of technologies, comprising an entire system of specially designed components which work together to provide a manufacturable, usable and salable system. The system is environmentally friendly, and uses a refrigerant composition which is free of chlorofluorocarbons (CFC). The refrigerant has low toxicity and low flammability. The system is therefore adapted to to effectively make use of these new refrigerants, as well as to drastically improve on the reliability of prior designs.

The new system includes a new, non-CFC refrigerant which allows effective and efficient cooling. Because of limitations in available coolants, this refrigerant composition has the ability, under certain circumstances, to cool to a temperature below freezing; therefore, the system is specially designed to distribute the coolant and the cooling effect so that freezing and frostbite are prevented.

The refrigerant is supplied in a standard aerosol-type canister which is self pressurized by the refrigerant. This canister is topped by an adapter, which allows detachable quick-connect coupling of the cryotherapy device, with minimal leakage. The canister is disposable or recycleable after use.

The coolant flow is controlled by an inject valve which connects to the canister adapter, and provides a predictable, controlled refrigerant flow to the cryotherapy adapter. The inject valve also allows rapid initiation of the cryotherapy by providing a "fast fill" feature. The inject valve also includes an integral check valve.

The refrigerant flows from the inject valve to the cryotherapy applicator through a tube. The tube, through a connector, enters into the applicator at the beginning of a serpentine flow path, specially designed to prevent pooling of refrigerant and to provide an even cooling distribution throughout the device, even under adverse conditions. The tube is specially sealed to the applicator to prevent leakage and to provide mechanical strength.

As the refrigerant vaporizes, it forms a gas, which exits the serpentine maze and inflates a bladder which surrounds the cooling portion of the applicator, providing a controlled, constant pressure to the tissue under treatment. The pressure is controlled by a combination pressure control and bladder vent valve, which is calibrated to 0.4 psi, a safe yet effective pressure. This combination valve sits in a custom fabricated flanged tube valve seat which has surperior resistance to failure and compatibility with the materials of the applicator for heat sealing.

The applicator is designed in a number of configurations, for human and veterinary use, to address the major accidental injuries encoutered by providing an anatomically conforming applicator with appropriate heat transfer characteristics. Configurations are also provided for body cooling, as is required in certain protective garb, e.g. Hazmat suits. In addition, the system provides a muscular conditioning system which allows improved performance and reduced musculoskeletal microtrauma. A scalp refrigeration system, designed to prevent cancer-chemotherapy induced hair loss is also provided. The cryotherapy system is also used in conjunction with medical monitoring and medical therapeutic devices, providing a combination therapy for both acute and chronic musculoskeletal injuries.

A peristaltic pump, activated by a sequential compression of portions of a subdivided bladder and controlled by a gas-driven sequencing valve, provides a system for circulation assistance.

The system is also applicable for portable refrigeration systems, such as for storage or transport of pharmaceutical solutions, beverages, or other liquids which are to be refrigerated but not frozen.

Various components of the system may also be used separately from the cryotherapy applicator:

1. the canister adapter may be employed an any aerosol-type canister which must be quick-connected to a continuous flow system, e.g. insect repellant.

2. the inject valve provides a precisely controlled flow for low viscosity fluids with a rapid flow bypass and intergral check valve.

3. the flanged tubular valve seat will find application in diverse instances where traditional molded flanged tubes have inferior properties, especially where the flanged tube is heat sealed.

4. the refrigerant in the canister, with the adapter and controlled flow inject valve, may be used to provide pressurized gas flow and/or spot cooling, for electronics uses, cleaning, degreasing, cryogenic topical anesthesia, and other purposes.

The present invention is a portable cryotherapy system which employs a novel pressurized refrigerant, contained in a disposable or recyclable canister, to provide a sustained cooling and super-atmospheric pressure in a bladder device which is provided around an injured body part. More particularly, the present invention involves a cryotherapy apparatus comprising a refrigerant-canister having an integral valve with a valve stem and a lip; a dome, mating with said refrigerant canister at said lip, having an aperture into which said valve stem protrudes; an inject valve, having means for mounting on said dome, means for activating said integral valve when mounted on said dome, a selectively activated passage having a high flow rate and flow-restricted passage allowing a low flow rate; a tube, mounted to said inject valve by a nipple inserted into said tube and locked by an external constrictor around said tube and said nipple; a maze, having a passage formed between two sheets sealed into a pattern having a plurality of blind ends in a plurality of orientations, said maze having at least one wall having a textured surface and receiving said tube at one end, and having an apparent cross-sectional area which increases with increasing distance from said tube; an expansion space, formed by a layer of material on one side of said maze, being parallel to said maze, into which an end of said maze distal from said tube empties; a flange, formed in a wall of said expansion space opposite said maze; and a pressure regulating discharge valve having a pressure regulating function and a selectively activated gas discharging function, mounted at said flange.

The use of a cryotherapy device in accordance with the present invention is effective in providing cryotherapy for secondary trauma treatment for humans and animals, is useful for reducing an individual's actual recovery time and related medical costs, and limits or prevents subsequent and often costly future complications in the case of serious injury. Additionally, the instantly disclosed cryotherapy device has the ability, when applied promptly, to reduce lost productivity time of workers who have suffered mild to severe sprains, strains and fractures.

In some instances, this reduction in lost employee productivity time is even greater. For example, in cases where early surgical intervention is indicated, the use of the inventive cryotherapy device can facilitate immediate treatment, rather than the typical delays of one or more days due to tissue swelling, thereby reducing the overall recovery time and expense while improving tissue survival.

The present invention provides particular advantages over a number of other cryotherapy systems. In the present system, controlled temperature and controlled compression is applied to prevent or treat secondary trauma. For example, the mere use of ice is ineffective since ice melts, thereby causing a buildup of water and requiring leak-proof systems or the reluctant acceptance of a system that leaks. Further, ice from a freezer usually starts at a temperature below 32 F., a temperature that may cause burns. Traditional bandages, administered to provide pressure, may slip or can be applied too tightly thereby resulting in negative therapeutic efficacy. Various cryotherapy devices heretofore available typically fail to provide controlled cooling, controlled compression or require significant capital equipment to operate.

The cryotherapy system according to the present invention employs ergonomic custom-designed cryotherapy devices, adapted for various body parts. The preferred embodiment includes a rugged, highly durable and reusable compression device that surrounds an injured body part. A refrigerant is released into the compression device, which then absorbs heat as it boils, causing an inflation of the device so that pressure (up to about 0.4 psi) and cold (about 36 F.) is applied to the injury. This therapy may be continued as long as is required, with possible replacement of the refrigerant canister if required.

In accordance with the invention, maximum pressure is applied in a manner that does not create a substantial risk of compartment syndrome, onset of which is generally considered to begin at an interstitial tissue pressure above 40 mm Hg. Therefore, the preferred pressure is between 21-35 mm Hg (0.4 psi). The pressure is applied so that an extravasation of fluid from capillaries in the area of the injury does not occur, and to help ensure that interstitial fluids are returned to the lymphatic drainage system. Thus, the pressure is an integral part of the treatment in accordance with the invention. The simultaneous application of pressure and cold also reduces the incidence of pain and shock.

As an additional embodiment, a known pulse oximeter system may be used in conjunction with the present cryotherapy system to assist in determining whether the tissue under treatment is receiving adequate blood circulation. Inadequate blood circulation typically results from too high an applied pressure or as a result of injury. Since oximeters generally measure the capillary circulation, they may provide an early indication of the onset of compartment syndrome (although skin perfusion may not correlate well with deeper tissues). Since the cryotherapy device according to the present invention is applied to injuries, and sometimes severe injuries, and the applicator portion of the device may obscure view of the tissues, the pulse oximeter may further be useful in determining tissue status and the severity of the injury.

In a preferred embodiment, the pulse oximeter sensor includes a phototransistor and LED pair which illuminate the skin below the cuff which determines blood oxygenation by differential light absorption at a plurality of wavelengths. The signals from the phototransistor are conveyed to a control system, which can, among other things, display oxygen saturation level or provide an alarm.

The present cryotherapy system may also be employed in conjunction with invasive and non-invasive, electric or electromagnetic stimulation devices. These stimulators may be used in the treatment of recalcitrant bone fractures (nonunions). Electric or electromagnetic stimulation may also be used to assist in the healing of fresh bone fractures. In addition, stimulators may be used as an adjunct to surgical spinal fusion procedures. Controlled cold and pressure aid in the reduction of postoperative pain, edema and blood loss. The attenuation of the inflammatory process may also improve healing.

One available stimulation device, the EBI Bone Healing System (Biomet Inc.), is a preferred device to be used in conjunction with the present invention. This system is non-invasive, and produces low-energy pulsed electromagnetic field signals that induce weak pulsing currents in living tissues, including bone, when such tissue is exposed to the signals. These signals are optimized by amplitude, repetition rate and duration to, Biomet claims, induce bone healing. The Biomet system further includes a control unit, which generates appropriate signals, and which may be powered by batteries (e.g. EBI Model 1020) or line current, and a treatment head which may be used proximate to the skin or displaced, such as through a cast or the present cryotherapy device. Treatment coils may also be incorporated in the cryotherapy device, especially flexible coils (e.g., EBI FLX Flexible treatment Coils). This treatment head emits electromagnetic pulses which induce pulsed currents around the fracture site. Thus, the present cryotherapy system may be used in conjunction with an electrical stimulation device like the Biomet device in order to assist in healing.

It is noted that the present cryotherapy system is also compatible with various types of electrical stimulation, which may be applied through the device, to the skin under the device, or fabricated as an integral part of the device.

The maze in the subject cryotherapy device is preferably cooled to about 36 F., a temperature which does not create a substantial risk of tissue freezing. The lowest temperature at any point at the surface of the bladder in contact with the tissue should be above 32 F., preferably above 35 F. The maximum temperature of the bladder In contact with the tissue is below ambient temperature, preferably at least 20 F. below ambient temperature, within the above constraints. The tissue cooling lowers the tissue metabolic rate, reduces inflammation, and reduces secondary inflammatory processes. Related to the lowering of the tissue metabolic rate, the oxygen demand of the peripheral tissue generally drops by a factor of two for each 10 C. drop in temperature (assuming that a shivering response is not evoked), thus lengthening the time for which oxygen-starved tissue may survive until the circulatory flow is restored. Thus, injured tissues which are treated with cryotherapy and localized controlled compression tend to be subjected to less tissue destruction secondary to trauma. The pressurized bladder also helps to stabilize musculoskeletal injuries and prevent additional accidental trauma to the injured site.

As a result of the use of second generation refrigerants, e.g. 134A and 124, the system in accordance with the present invention is designed to prevent any localized volatilization of a substantial quantity of refrigerant fluid, since such volatilization withdraws heat in tissue that is proximate or adjacent to the system. Therefore, in contrast to prior systems using conventional CFC refrigerants, the present system must carefully control and limit the quantities of refrigerant flowing to the cryotherapy device. Thus, in one embodiment according to the present invention, the refrigerant composition is a ternary mixture of refrigerant liquids, having a greater proportion of highest-boiling component than lowest-boiling component and than mid-boiling component. In general, the lowest concentration will be the mid-boiling component, while the other components may be approximately equal in concentration. This is believed to provide a system in which the lowest boiling component cools the highest boiling component, and creates a reservoir of low-temperature material, which helps to maintain a low temperature.

The materials used for the apparatus herein are preferably selected to be compatible with each other and with the refrigerants. Therefore, polyurethanes and nylons are preferred. The materials, especially in locations subject to heat sealing or bonding should not have any coating or residues on the surface which are incompatible with the chemistry of the process of administration of cryotherapy or the sealing process. Likewise, coatings may be applied which improve the surface properties of the materials for the joining process.

More particularly, the inject valve body and the discharge valve body may both be formed of Nylon 101. O-rings, where necessary, may be formed of buna-n rubber, although other compounds which are compatible with the refrigerants are also available and within the scope of the invention.

The novel refrigerants employed in the present invention preferably do not include conventional chlorofluorocarbons (CFC's), which are believed to destroy the ozone layer, and are therefore the subject of an international ban, with limited exceptions. Rather, the refrigerants include second generation fluorocarbon/hydrocarbon refrigerant fluids such as the mid-boiling components 142B (BP around 14.4 F.) and 124 (BP around 12.2 F.), the low boiling components 152A (BP around −11.5 F.), 143A, 125, 23, OZ-12 and 184A and the high boiling component 123 (BP around 82 F.) in a compatible mixture. See Du Pont Fluorochemicals, AG-2 ENG (October 1992). The refrigerants alone and in combination are preferably selected so that they are relatively non-toxic. Of course, any gas (other than oxygen) poses the risk of asphyxiation, and the cryotherapy system preferably includes an accidental refrigerant release prevention system. The known mid-boiling freon refrigerant fluids have a boiling point around 3.8 C. (39 F.) or above, while the second generation mid-boiling fluids generally have lower boiling points. The present refrigerant mixture preferably contains about equal proportions of 152A, 142B and 123, although each may range from about 15–40% of the total, preferably with between 33–40% of the high boiling component, which acts as a heat transfer agent in the maze.

Therefore, in contrast to prior systems relying on relatively high boiling point fluids, the absorption of heat of vaporization of the present fluids must be spread over a large area of the bladder to prevent tissue freezing. In addition, assuming that the cryotherapy system is in steady state at the desired 36 F., the known refrigerants will tend to self-regulate at the desired temperature, while the new non-CFC refrigerants will have no such stability. While it is preferred that the refrigerant directly absorb heat from the tissue and through the walls of the maze, the systems according to the present invention may also include the use of a highly thermally-conductive heat sink structure which is in turn cooled by the refrigerant. The refrigerant mixture in the disposable canister should not fractionate, so that through the expenditure of the contents of the canister, the refrigerant mixture remains such that the low-boiling component expels the mid- and high-boiling components and precools the mixture. Thus, the low-boiling component should not be reduced during use to such an extent that an insufficient amount of refrigerant flows from the canister. This allows the flow control system to operate without change over the course of a treatment. Of course, an external propulsion system, such as a compressed gas in a bladder within the canister, could be used to reduce the need for the low boiling component, thereby increasing the amount of mid-boiling component which may be provided.

The present system is preferably used on human or equine injuries. While a variety of human injuries are addressed herein, the present system also is useful for the treatment of newly-acquired and pre-existing limb injuries in horses, both prior and subsequent to competition. Statistically, about one in four horses suffers limb injuries during a race, and subsequent racing is limited by the healing rates of the injury. Therefore, any method which reduces the amount of injury and promotes healing of existing injuries is desirable. The present system, because of its portability and ease of storage, may be immediately available at race tracks to thereby minimize secondary trauma through the rapid and simultaneous application of pressure and cold to the injuries which will thereby promote more rapid healing.

The present invention also finds application in the pre-exercise conditioning of muscles in order to decrease the likelihood and extent of injuries that occur during exercise. Likewise, after exercise, the application of the cryotherapy device will decrease the effects of any microinjury that has occurred during exercise. With respect to horses, it is known that equine lower leg vasculature and circulation are generally inadequate for the stresses that man applies while racing the horses, and therefore competitive and noncompetitive exercise, even without overt injury, may produce significant microtrauma to these animals, a condition generally treatable by use of the instant invention.

The present invention preferably employs a standard aerosol-type canister, which is used in conjunction with a special adapter. As applied to the present cryotherapy device, however, the refrigerant is not applied as a propellant, but rather uniquely as a working constituent. The adapter prevents inadvertent access to the valve stem, provides secure affixation of the inject valve, and allows interruption of the treatment without significant loss of refrigerant. Thus, in a specific embodiment, the adapter, having an annular rib, snaps over an annular lip of the can, while providing an interrupted ½ turn lockable screw thread mount for the inject valve, which depresses the valve stem when mounted. In such an embodiment, the valve stem is recessed below the top of the dome.

The adapter according to the present invention may also be used in any application (other than cryotherapeutic) where a secure attachment of a secondary control or valve is desired to be affixed to a standard aerosol-type canister. For example, it may be used to emit a bug spray as a fog, or to supply a lubricant or coolant to mechanical member, such as a machined part.

BRIEF DESCRIPTION OF THE DRAWINGS

The invention is shown by way of example in the drawings, in which.

DETAILED DESCRIPTION OF THE PREFERRED EMBODIMENTS

Figure 1A:
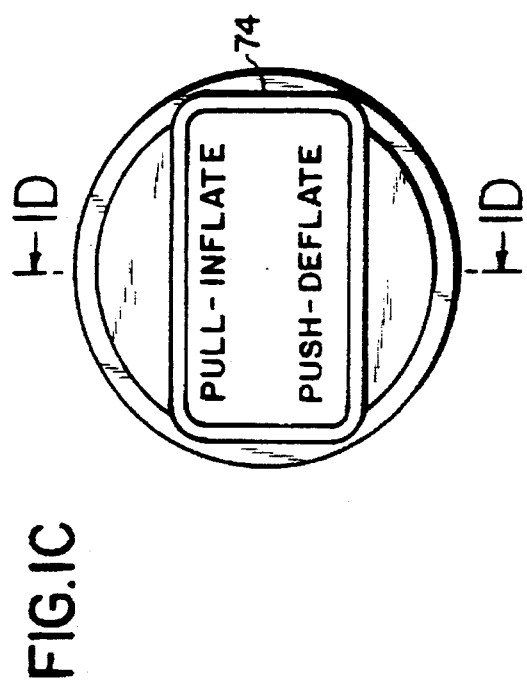
FIGS. 1A and 1B are top and cross sectional views of a push to inflate exhaust valve.

The present pressurized cryotherapy devices may be preferably adapted to fit various parts of the human or animal body, including the head (e.g. a headband), shoulder, forearm, elbow, wrist, hand, lower back, thigh, knee, patella, calf, ankle and foot for humans. The pressurized cryotherapy devices according to the present invention may be further adapted for use as a tri-dimensional skull cap (pre- and post-cancer chemotherapy treatment and migraine headaches), cervical collar, facial compress (pre- and post-cosmetic surgery treatment), full arm extension, hip joint applicator, and full leg device. The cryotherapy device is designed so that the surface closely approximates the anatomical surface to which it is applied, for a proper fit, and such that an increased pressure is evenly applied to the tissue.

In a preferred embodiment of a full leg cryotherapy device, an elongated cooling pad is provided with a straight line enclosure with a patella closure. Likewise, a full arm cryotherapy device is provided with a straight line enclosure with an elbow closure.

A shoulder-chest embodiment covers the body from the sternum to spine and from the top of the shoulder to well below the shoulder blade and down the arm to the elbow. A vest system preferably covers the chest and upper back. The shoulder-chest embodiment is preferred for sports-related injuries, such as throwing arm injuries, while the vest is preferred for pre- and postoperative cryotherapy, especially using a recirculating refrigerant system. The portable system may be used in conjunction with hazmat protective clothing, without a pressurized bladder being operative.

The present invention also provides a system and method for providing effective portable cooling and pressure for various purposes. These include drug storage and hazardous material transport. For example, insulin dependent diabetics often travel with insulin. This insulin should be cooled to between 39 and 70 F., in order to prevent degradation and ensure potency. However, under hot conditions, the ambient temperature is higher than the recommended storage temperature. While it is known to use a freezer-activated cooling device to cool the insulin, this requires that periodically a freezer be available. The present system, when adapted by miniaturization and the provision of external insulation, may provide a long term cooling solution which does not require access to a freezer. Likewise, where hazardous, heat sensitive materials are to be stored or transported, the present system allows for cooling for a prolonged period. Further, the present system may also be used to cool beverage cans, foods and other comestibles. In these examples, the controlled pressure is not necessary, however it ensures firm contact and assures good heat transfer from the object(s) to be cooled and the maze. In these instances, the exhaust valve may be replaced with a restrictive aperture, because a controlled relief pressure is not necessary. Likewise, the fast fill feature provided in a medical or veterinary therapy embodiment according to the present invention to rapidly establish normal operating conditions in the device by allowing a rapid flow of refrigerant from the inject valve into the heat transfer portion of the cryotherapy device may be unnecessary. The refrigerant composition and maze system, though adapted in shape and form, may be essentially identical. It is noted that in many instances, it is important that a refrigeration system not cool to temperatures below freezing. The present system provides a simple, reliable and portable solution to this problem, which does not require electrical power, batteries or a secondary refrigeration system with a heat accumulator.

The disposable canisters preferably contain a mixture of 124, 153 and 142B refrigerants, provided for portable human emergency use preferably in a 4, 8, 17 or 25 oz. canister, respectively yielding a number of treatments dependent upon the circumstances of use. For other applications, the size of the canister may vary, up to about 35 lbs, where portability is less important than economy, and many treatments will be conducted with the device.

The canister may be provided with a quantity remaining indicator. This indicator may be a liquid crystal strip, applied axially to the wall of the canister, responsive to a change in temperature in the wall of the canister due to the presence or absence of refrigerant fluid on the other side of the wall. This strip preferably displays differential temperatures over a broad range of temperatures, as may occur when the canister is venting, producing low temperatures, and when the canister is being stored, where high temperatures may occur. This latitude may be provided by providing longitudinally spaced strips of liquid crystal thermometric material, each strip having a different temperature band. The quantity remaining function may also be provided by a mass sensor, acoustic or resonant frequency sensor, dipstick, or other known type of sensing system.

The cryotherapy device according to the present invention may be used for veterinary, especially equine applications. The cryotherapy applicator is designed for application to either the ankle, hock or cannon bone, or the entire leg of the horse. The preferred canisters for use in veterinary applications are 25 oz. and between 3–5 lbs. In some veterinary applications and in fixed clinical applications, larger containers of refrigerant may be employed. When large containers are employed, it is preferred that a timer or automatic cutoff system be provided in order to prevent accidental over-treatment of a patient or waste of refrigerant. Further, large containers pose an increased risk of asphyxiation, and therefore the system must prevent unintended leakage and the canister must provide resistance to failure during adverse conditions, e.g. dropping, small fires, etc.

The present invention may also be applied to cool pharmaceuticals, comestibles and chemicals. For example, insulin is a drug which is preferably stored at temperatures between 39–70 F. However, travelers may be subject to sustained temperatures in excess of 70 F., which may degrade the drug resulting in reduced potency. The present cryogenic system may be applied to apply controlled refrigeration to the pharmaceutical. Since the quantity of drug to be stored is generally small, and efficient insulation may be applied around the system, a miniature efficient system is possible. Since the application of pressure is not critical, the exhaust valve may be replaced with a simple restricted flow aperture. Further, the inject valve need not include the fast-fill feature provided in a preferred medical treatment embodiment according to the present invention to rapidly establish operating conditions. Known systems are available which provide a heat extraction element which must be stored in a freezer prior to use. These other systems therefore require periodic accessibility of a freezer. A further application of the present system is in a cooling system for transport of hazardous materials and other goods which are perishable or require cooling. Such a system must have a refrigerant reserve which allows extended safe usage.

A system for cooling comestibles, such as consumer and institutional beverage, including soda and beer cans, wine bottles, and other potable liquids, e.g., water, milk, baby formula, may also be constructed according to the present principles. A can may be inserted in a sleeve, which includes a refrigerant maze, through which the refrigerant passes. The sleeve preferably inflates, causing close contract between the sleeve and the can. The refrigerant canister preferably includes enough contents to cool a number of cans, e.g. each of six cans from 80 F. to 40 F., and cools each can in about 1–5 minutes.

The present system may also be used as a portable refrigeration system for other types of foods. As stated above, the pressure in a system designed other than for cryotherapy need not have an accurate pressure relief valve and need not include a fast fill feature, as immediate establishment of operating conditions is likely not critical in these applications. However, with aqueous systems, such as pharmaceutical solutions and foods, it is important that the temperatures remain above freezing.

The preferred cryotherapy device is a heavy duty, long-lasting, structure. In the event that the device is expected to be subject to or at risk of contamination, a disposable liner may be supplied which surrounds the device. The liner is constructed so as have an insubstantial effect on the heat transfer from tissue to the maze, and to allow venting of refrigerant gas from the exhaust valve. The outer liner may be formed of flexible plastic or elastomeric film. The liner preferably has a seal, such as a "zip-lock" seal, or is sealable, in a manner which provides for entrance of the umbilical tube through the sealed portion and a vent aligned with the exhaust valve which diverts released gas out of the liner.

Under certain circumstances a disposable device, with or without a liner is preferred. For example, where the unit is likely to become covered with blood or other contaminant, is expected to be abused or risks puncture, a disposable device is preferred. A disposable device may also be preferred if there is a risk of theft or return of the device after use is impractical. The disposable unit differs from the heavy duty unit by being made by a cheaper, less durable process, designed for a shorter life cycle of a limited number of treatments. Thus, while a preferred, heavy duty embodiment consists of layers of polyurethane-covered nylon, a disposable embodiment might be fabricated from polyurethane sheet or reinforced polyurethane sheet. Indeed, other materials may be used, even those which are less compatible with the refrigerants. Likewise, the heavy duty embodiment includes a fast-fill function in the inject valve to rapidly cool the maze of the heat transfer portion of the device and to fill the bladder to operating pressure, while a disposable unit might forego this feature with a delayed achievement of steady state conditions. A heavy duty embodiment includes a replaceable discharge valve, with a variety of available pressures, while a disposable embodiment might have a permanently-installed discharge valve.

The device according to the present invention is preferably sterilizable, especially where the device is applied in emergency situations where blood contamination may occur or where the device is to be applied in proximity to an open wound.

The refrigerant passage-containing device of the present system is formed of a urethane coated nylon cloth (denier, for example) which is formed into a maze, having a plurality of blind pockets that form traps of varying orientation, by the use of radio frequency sealing, into specific patterns that allow for contour placement of the device over and/or around the injury sites. The Nylon cloth is preferably between 100–1000 denier. The nylon is most preferably 200 denier, with a water repellant outer finish. The radio-frequency sealing process joins two or more sheets in parallel planes by passing a radio-frequency or microwave signal through the layers, causing localized heating in the layers in a pattern conforming to the antenna-applicators. If materials other than urethane are used, then other known sealing or fusing the layers may be applicable. These methods include heat sealing, adhesives, pressure sealing, sewing and the like. This localized, patterned heating from an RF sealing process causes the polyurethane coating of the nylon mesh to fuse with adjacent layers. On cooling, the fused portions form a hermetic-type seal, which is adequate to contain the refrigerant as a liquid and as a pressurized gas. The polyurethane coated nylon material has a low compliance, so that once the device is filled with refrigerant, further Input of refrigerant will expel substantially the same amount of refrigerant through the pressure relief valve.

After the heat transfer portion of the device is placed proximate to the injury site, refrigerant is injected to rapidly to cool the maze to operating temperature, e.g. about 36 F. The injected refrigerant fluid vaporizes in the maze, to rapidly cool the device and tissue. Thereafter, the, rapid injection of refrigerant is stopped and fluid slowly flows into the maze, wherein it vaporizes, absorbing heat in the process, to maintain the desired cool temperature. The maze terminates in a port which empties into a bladder, which allows the gasified refrigerant to fill a space distal from the maze with respect to the tissue. A pressure regulating valve allows the gas to escape from the bladder, maintaining a predetermined positive pressure in the bladder. The temperature preferably achieved when the device is in use is around 36 F., and the predetermined pressure is preferably around 0.4 psi or 21 mm Hg. Alternatively, a pressure relief valve can be provided which allows pressures of about 30 mm Hg and 35 mm Hg. Of course, a pressure relief valve may be provided having any desired relief pressure, the preferred maximum for biological tissues being 300 mm Hg, being effective for arterial occlusion. The 21 mm Hg pressure is preferred for over-the-counter available devices, while 30 and 35 mm Hg pressure relief valves are preferably available for use under medical supervision.

With the exception of the canister and valve components, it is preferred that the various components of the cryotherapy system be formed of non-metallic components so that the device need not be removed for X-rays. Thus, the device may be applied immediately after an injury, and maintained in place until other therapy is begun. Thus, the cryotherapy system according to the present invention may be incorporated in fixation devices for chronic therapy, and may be used in conjunction with other diagnostic or therapeutic modalities. In the case of a cast device, the maze portion is applied proximate to the skin, optionally with a thin absorbent pad between the maze and skin to facilitate evaporation of sweat. The cast is applied with the bladderr empty or partially or fully inflated, to allow use of the device without Inappropriate pressure buildup and to allow proper functioning. The cryotherapy device should be situated avoid interference with the fixation function of the cast. Further, the exhaust valve is placed accessible through the cast, without substantial flow restriction. The exhaust valve is preferably mounted on a flange fixed to the cast.

The refrigerant is preferably a fluorocarbon-based coolant mixture. The mixture is preferably a ternary mixture of components, with the mid-boiling component as least prevalent and the highest boiling component equal or greater in quantity than the lowest boiling component. However, any refrigerant or refrigerant mixture may be used which, under the circumstances of use, is relatively non-toxic, has low flammability, has a high specific heat of vaporization, is environmentally acceptable, does not adversely affect the materials of the device, and has a characteristic which allows the maze to be cooled to a stable 36 F. The choice of refrigerant will also be dictated by the availability of a recycling system for the refrigerant, and cost sensitivity.

The change in inflation pressure is preferably delivered by changing the exhaust valve itself, which has a fixed, calibrated relief pressure. Of course, the pressure relief valve function of the exhaust valve could be a variable pressure type, possibly with an electronic control system. A variable pressure relief function may be obtained by providing a helical thread and follower to alter a spring tension applied to a ball in a valve seat. A turning of the helical thread will therefore alter the relief pressure, and the relief pressure may be calibrated to the rotational angle of the thread.

An electronic pressure relief valve preferably employs a solenoid valve which is activated by a control, based on a pressure sensor. The pressure sensor need not be located at the relief valve location, thereby allowing the system to compensate for various intervening structures which might alter the pressure seen at the valve as compared to the pressure seen by the tissue. The tissue pressure is presumed to be the relevant factor. The electronic control may also be used to provide an alarm indication if the relief valve malfunctions, or if the tissue pressure is high despite a relief of pressure in the bladder. It is also noted that if a single electronic control may be used for the entire device, and therefore all aspects of the operation of the device may be integrated and controlled together. An electronic control is especially preferred for chronic treatments where portions of the cryotherapy system may be obscured from view and unattended operation is desired. The electronic control system is also preferred where the device is used under medical supervision to provide aggressive therapy, i.e. therapy which, unless carefully monitored, might be hazardous. Thus, the control system may carefully control temperature, pressure and treatment cycle, and may further allow programmed mid-treatment variations in temperature and/or pressure. Further, the use of condition feedback sensors and biofeedback sensors may also allow customization of the treatment for the patient, while ensuring safety.

A recirculating closed-circuit refrigerant unit may be employed, especially where extended treatments are desired, multiple patients are subject to treatments or portability is not necessary, such as in a hospital or clinic. Under such circumstances, since the coolant is not released into the atmosphere, a CFC, e.g. Freon® may be employed, particularly under an exemption granted for medical devices to allow use of CFC's. A compact electrically driven compressor or thermoelectric cooling device is preferably provided to reliquify the refrigerant. In a closed circuit refrigeration system, the lowest boiling component may be substantially reduced or eliminated, because an active pumping system may be used and the precooling function may be provided by the condenser system. However, a CFC need not be used, and the present refrigerants provide a useful and effective alterative.

EXAMPLE 1

The disposable canister 1 is provided with an adapter 2, which is designed to operate in conjunction with the inject valve 3. The adapter 2 fits atop a standard-type aerosol can, providing access to the standard valve stem 4 via a deep narrow recess 5 to prevent accidental or intentional misuse. The adapter 2 also allows stacking of the canisters. The canister adapter 2 has an undercut lip 6 to hold on to the edge of the coolant canister dispensing valve. The adapter 2 is designed for one time use, or it may be reused on a new or recharged canister 1. When the undercut lip 6 snaps over a portion of the valve cap 8, it is distorted into a positive lock through a full revolution. Thus, after mounting on the canister 1, the adapter 2 is rotationally stable with respect to the axis of the canister 1, while remaining securely in place. On the outside of the adapter 2 is a ½ turn interrupted helical thread 9 that provides a positive lock when the inject valve 3 is attached. The inject valve 3 is attached by aligning a female helical thread 10 on the bottom of the inject valve 3 with the male helical thread 9 on the top of the adapter 2. The inject valve 3 is then rotated with respect to the adapter 2, thus engaging the mating threads. The inject valve 3 female thread 10 includes a locking nub 11 for each thread 10 portion, so that when the threads are fully engaged, the locking nub 11 engages the bottom-most portion of the thread 9 of the adapter 2, locking the two together. The central post 12 of the inject valve 3, when mated to the adapter 2, depresses a stem 4 of the canister valve, allowing flow of refrigerant 13 from the canister 1 to the inject valve 3. The central post 12 of the inject valve 3 is provided with snug enough fit so that there is no leakage around the central post 12. Sealing may be improved by use of an O-ring 14, which fits between the central post 12 and the canister valve stem 4.

The inject valve 3 is removed from the canister adapter 2 by applying a torque to the inject valve 3 with respect to the adapter 2 in the opposite direction from the insertion twisting, which causes the locking nub 11 to disengage the bottom-most portion of the thread 9 of the adapter 2. The inject valve 3 is then rotated with respect to the adapter 2 to disengage the two. Upon axial displacement of the inject valve 3 from the canister adapter 2, the canister valve 15 is allowed to close, thereby preventing venting of refrigerant 13, if any remains in the canister 1.

The inject valve 3 preferably also includes a check valve function to prevent back-flow from the heat transfer portion of the cryotherapy device 16, and to allow mid-treatment replacement of the refrigerant canister 1 without substantial interruption of therapy. This function may be advantageously be provided by use of the same ball 17 used in conjunction with the fast fill feature, which seals, under conditions of reverse pressure, against an opposingly placed second conically tapered orifice 19 from the first conically tapered orifice 18 employed by the fast fill feature. Thus, in its resting position, the ball 17 blocks the fast fill passage 20, being pressed against the first conical orifice 18 by the pressure of the refrigerant 13, which exceeds a spring tension of a retaining spring 21. A manually operable push button 22, having an extension 23, displaces the ball 17 from proper seating against the first cortically tapered orifice 18 to provide the fast fill feature. When depressed, the extension 23 pushes against the ball 17, allowing refrigerant 13 from the canister 1 to flow into the umbilical tube 24 and then to the normal operating normal operating conditions, if the pressure in the tube 24 leading to the cryotherapy device 16 is greater than the pressure seen by the ball 17 from the direction of the canister 1, such as when the canister 1 is removed during therapy, the ball 17 will assume a position against the second conically tapered orifice 19 and prevent backflow. The normal flow rate of refrigerant 13 in the cryotherapy device 16 is established by one or more drilled orifices 26 in parallel with the first conically tapered orifice 18. These drilled orifices 26 preferably do not bypass the second conically tapered orifice 19, so that the check valve function operates on this bypass flow path as well.

The adapter 2 has a dome shape 27 on its upper surface 28, and has an annular rib or lip 6 on its lower surface 29 which snaps over a corresponding annular lip 7 of the refrigerant canister 1. The adapter 2 has a central elongated orifice 30, which when mounted on the canister 1, extends above a valve stem 4 protruding from the top of the canister 1, to prevent accidental activation and to facilitate stacking and shipping of the canisters.

EXAMPLE 2

The inject valve 3 according to the present invention mates to the canister adapter 2, providing a sealed path from the canister valve 15, through the inject valve 3, to a piece of tube 24 which connects the inject valve 3 to the heat transfer portion of the cryotherapy device 16. Thus, the inject valve body 31 mates to the ½ turn interrupted screw thread 9, and connects easily. The ½ turn thread 9 causes the inject valve 3 to move axially toward the canister 1, and locks in place. The inject valve 3 includes a hollow cylindrical central post 12 which protrudes downward, concentric and outside the valve stem 4 of the canister 1. The stem or central cylindrical post 12 of the inject valve 3 depresses the valve stem 4 of the canister 1, releasing its contents, the refrigerant 13. An O-ring 14 provides a seal so that the refrigerant 13 does not leak around the inject valve 3.

The inject valve 3 comprises two flow paths. A first flow path provides a predetermined steady flow rate of coolant, which is sufficient to provide steady state cooling of the cryotherapy device 16. This first flow path is preferably formed by one or more narrow orifices 26 in a plate, although other configurations may be acceptable. The orifices 26 may be formed by laser drilling, electron beam drilling, insertion of a calibrated-orifice containing member in the plate (e.g. jeweled orifice), a glass capillary tube, or other known means. In the present embodiment, the preferred orifice is about 1–6 mm in length and 0.006" in diameter, the diameter being precisely controlled, but the diameter of the orifice 26 is defined by the refrigerant 13 mixture.

The second flow path, part of the fast fill feature, is selectively activated by an external button, called the fast fill button, which is the inject valve pushbutton 22, to provide an immediate injection of a large amount of refrigerant 13 to quickly initiate the therapy and cool and inflate the cryotherapy device 16. This second flow path is preferably formed by a ball 17, resting in the first conical tapered orifice 18. The ball 17 is normally pressed against the tapered wall of the orifice 18 to seal the orifice 18 by the internal pressure of the refrigerant in the can. The externally accessible inject valve pushbutton 22 has an extension 23 which displaces the ball 17, thereby allowing a flow of refrigerant 13 to pass. Spring 21 returns the pushbutton 22 to its upright, non-functioning position. The first and second flow paths are parallel, thus the net flow of refrigerant 13 is the sum of the constant flow through the first path and the selective flow through the second path.

Alternatively, the first flow path may comprise a system for ensuring a predetermined amount of leakage around the ball 17 of the second flow path, although this is not preferred due to the difficulty of controlling the static flow rate and possible difficulties in quality control.

An electronically controlled embodiment may include a solenoid or piezoelectric valve 33 which acts in pulsatile fashion to establish the steady state flow condition. This pulsatile flow may be purely time based, or may be regulated by a sensor 34 to assist in temperature regulation in the maze 25. Such a temperature regulated device provides a temperature sensor 34 near the entrance of the umbilical tube 24 to the maze 25, which is presumed to the coldest portion of the maze 25. The coldest portion of the maze 25 preferably remains at 36 F.

EXAMPLE 3

An overcap 35 is preferably provided to prevent the inject valve pushbutton 22 from becoming lost. The overcap 35 is sealed to the inject valve body 31 by means of ultrasonic welding. The overcap 35 also includes a "V" type clip 36 which fits over the umbilical tube 24 which carries the refrigerant 13 from the inject valve 3 to the cryotherapy device 16, thereby preventing accidental disconnection of the tube 24. The retaining structure including the "V" type clip 36 also prevents catastrophic results from a kink in the tube 24 by ensuring that the flow path does not fail if the flow is temporarily blocked. The tube 24 is preferably a ⅛" ID Tygon® or polyurethane tube, which is inserted around a hollow stem 37 protruding from the side of the inject valve body 31.

EXAMPLE 4

The inject valve 3 valve body 31 includes a ball seat 38. The ball seat 38 has a number of functions. First, it retains the ball 17 which is displaced to provide the fast fill feature. Second, it holds a rubber O-ring 39 which prevents leakage when the ball 17 is seated and the fast fill feature is not activated. Third, the ball seat 38 has one or more narrow orifices 26 drilled vertically through it to provide a normal, e.g. steady state, flow path. These orifices 26 are each about 0.006" diameter, although this will vary with the refrigerant 13 mixture used. The diameter of these orifices 26 is precisely determined to control the steady state flow rate and provide a constant temperature in the maze 25. The normal flow rate is generally predetermined, and devices which require differing steady state flow rates are modified by varying the number of orifices 26 bypassing the fast fill valve ball seat 38. It is also possible to vary the flow rate by varying the diameter of the orifices 26, although this is not preferred. The number of orifices 26 is therefore determined by the size of the heat transfer portion of the cryotherapy device 16 and the expected cooling capacity which will be necessary to maintain the proper temperature.

A retaining ring 40 is provided to hold the O-ring 44 in the ball seat 38 cavity, and preloads it. The retaining ring 40 reduces wear and seals around the canister valve 15.

A stem-like extension 23 is provided projecting from the inject valve pushbutton 22 which displaces the ball 17 from the ball seat 38 when the inject valve pushbutton 22 is depressed. The force of the stem-like extension 23 acts against the pressure of the refrigerant and a return spring 21, provided on the other side of the ball 17, returns the pushbutton to its original, upright position.

A diaphragm 41 is formed in conjunction with the ball seat 38. The diaphragm 41 prevents leakage of refrigerant 13 around the stem-like extension 23 and out of the inject valve 3 when the inject valve pushbutton 22 is depressed. The diaphragm 41 is held in place by a retaining ring 42, which is a star washer pressed into the cavity 43 of the inject valve body 31 to retain the diaphragm 41.

The backflow prevention function, as stated above, is provided in the inject valve 3 and employs the same ball 17 as the fast fill function. When the pressure in the inject valve 3 distal to the ball 17 exceeds the pressure proximal to the ball 17, i.e. the pressure on the canister 1 side of the pressure applied by the return spring 21, is less than the pressure in the umbilical tube 24, then the ball 17 is displaced in the opposite direction to occlude a second cortically tapered orifice 19.

EXAMPLE 5

The refrigerant fluid is transmitted through an umbilical tube 24 from the inject valve 3 to an inject port 46 of the heat transfer portion of the cryotherapy device 16. From the inject port 46, the refrigerant 13 follows a maze 25 pattern formed by three sheets, two polyurethane sheets 47, 48 and a polyurethane impregnated nylon cloth sheet 49. Of course, the two polyurethane sheets 47, 48 may be replaced by one thicker sheet, or a larger number of thinner sheets. The maze 25 pattern is fabricated by placing the sheets 47, 48, 49 parallel to each other and RF sealing them together by means of a die, the sealed portions 58 being caused heating the die and the polyurethane polymer by applied RF energy, having a pattern corresponding to the desired maze 25 pattern. The heat causes a partial liquification of the polyurethane of the sheets 47, 48, 49 which results in fusion and sealing upon cooling. The maze 25 pattern provides blind pockets 51 in varying orientations, so that any refrigerant 13 liquid is distributed over the entire maze 25, both under static conditions and when the cryotherapy device 16 is shifted. Thus, any particular orientation of the cryotherapy device 16 or any random tilting or vibration of the cryotherapy device 16 will not result in substantial pooling of refrigerant 13 in any portion of the cryotherapy device 16.

The inner surface 52 of the polyurethane sheet 48 which faces the polyurethane coated nylon sheet 49 has small cylindrical protrusions, ribs or an interrupted spline longitudinally placed, i.e. with a long dimension parallel to the expected flow with respect to the maze 25, which protrude into the refrigerant 13 flow path. These surface features 53 may be formed by heating the sheet while it is placed under pressure in a die, having a corresponding pattern formed on its face. The second polyurethane sheet 47 is sealed parallel to the polyurethane sheet 48 with the surface features 53, and outside the refrigerant 13 flow path, for added wall strength.

The surface features 53 are herein referred to as turbulators. while these turbulators are not necessary in all circumstances, and indeed their function may be accomplished by the convolutions of the walls 54 of the maze 25 pattern, where the maze 25 is large and the maze pattern includes relatively long runs, the inclusion of turbulators is preferred. As stated above, the turbulators are preferably provided on the polyurethane sheet 48 wall of the maze 25, and serve to decrease laminar flow and increase turbulent flow in the maze 25. Turbulent flow promotes vaporization, and by providing dispersed turbulators throughout the flow path, temperature variations in the maze 25 are minimized. In addition, these surface features 53 have a second function, that of maintaining a flow passage in the maze 25 even if the cryotherapy device 16 is flexed or folded, thereby preventing a backpressure buildup and possible device failure.

The protrusions, ribs or interrupted spline provided as the surface features 53 are provided such that flow will be maintained even if the maze 25 is bent 90 degrees over a 1 cm diameter rod. The protrusions of the surface features 53 should protrude about one-quarter to about one-half the apparent diameter of the lumen of the maze 25. Ribs, if provided, preferably run parallel to the maze 25 pattern, and are about 3 mm long with an interruption of about 1.5 mm.

The turbulator elements are preferably located no further apart than about the apparent diameter of the lumen of the maze 25 at that point. Sharp turns, e.g. about 90 degrees or greater, may be used or applied instead of protrusions as the turbulators for generating turbulence. The longest straight path of the maze 25 should be no longer than about ten times the apparent diameter. The path layout is designed to be such that the maze 25 will allows removal of about 2 cal/min per 10 square centimeters of maze 25. The optimal heat removal rate, however, will depend on a number of factors, such as ambient temperature, external insulation, tissue temperature, heat production and heat capacity, humidity, and other factors.

The refrigerant 13 path is thus defined by the maze 25, with the walls maintained separated by the protrusions or ribs to help maintain patency of the lumen. The maze 25 has a cross sectional area which increases in tapered fashion as the refrigerant 13 progresses through the maze 25. The velocity of the refrigerant 13 will tend to remain constant or increase slightly due to vaporization of the refrigerant 13 and the pressure necessarily decrease, thus causing or allowing flow through the maze 25. The maze 25 is preferably formed by a flow path having a width of about 1.0 to 1.6 cm minimum between sealed portions 58, with a gradually enlarging taper along the flow path to a size having an inflated cross section about one and one-half times larger than that of the inlet portion cross section. The maze 25 has a series of pockets, blocking any straight path, which serves to distribute the volatilizing refrigerant throughout the maze 25 and prevent liquid refrigerant 13 from discharging directly to the exit of the maze 25, by means of gravity (orientation), vibration, or by means of a sudden increase in pressure.

The maze 25 includes a single flow path which leads from the umbilical tube 24 to the bladder 55. The maze 25 follows a serpentine path which provides a plurality of spaces, the blind pockets 51, for the accumulation of refrigerant 13 fluid, having orientations so that fluid will be trapped no matter which orientation the cryotherapy device 16 obtains. The sealed portions 58 of the walls of the maze 25 preferably have a width of about from 0.12–0.16 inches, with any ends having a curved edge and a diameter of about 0.18 inches. The path is designed so that the coolest path, that near the inlet to the maze 25, is proximate to the warmest path, that near the exit of the maze 25, and that the inlet path is in the middle of the cryotherapy device 16.

The paths in the maze 25 are preferably oriented so as to be 45 degrees from a fold line or the longitudinal axis, e.g. the limb axis, of the cryotherapy device 16, thereby minimizing the risk that the maze 25 will be bent or crimped along a natural fold of the cryotherapy device 16 to occlude flow.

The maze 25 terminates in an expansion space, e.g. a bladder 55, which is preferably substantially coterminous with the area of the maze 25, but having a larger lumen size and less defined flow path. The bladder 55 is formed by a fourth sheet, consisting of polyurethane coated nylon cloth 50, which is RF sealed to the maze 25 in a second operation. The fourth sheet 50 is preferably sealed to the maze 25 only about its periphery, but may also be subdivided into smaller bladders, preferably sealed to the maze 25 at points aligning with the maze 25 pattern. Thus, the expansion space of the bladder 55 may be a single pocket, or be subdivided. The bladder 55 provides a reservoir of gas to apply the desired pressure to the injury. This bladder 55 is preferably on the outer surface of the cryotherapy device 16, e.g. away from the tissue, and provides insulation of the refrigerant 13 in the maze 25 from the external environment, helping to ensure that the cooling action is directed primarily to the injury. The bladder 55 is pressurized to about 0.4 psi, which is controlled by the exhaust valve 56 having a pressure relief function.

The tube 24 which supplies refrigerant 13 to the maze 25 is sealed to the maze 25 by means of a plastic sealing band 57, disposed between the two layers 48, 49 forming the walls of the maze 25, e.g. the polyurethane coated nylon cloth 49 and the polyurethane sheet 48 having the surface features 53, facing the polyurethane-coated nylon cloth 49.

EXAMPLE 6

At a portion of the expansion space, somewhat displaced from the terminus 59 of the maze 25, an exhaust port 60 is located. This exhaust port 60 is displaced in order to limit a direct flow. The exhaust port 60 includes a flange 61 which is formed of a material which is compatible with the polyurethane coating on the nylon sheet 50. This compatibility includes compatibility with the RF heat sealing operation to attach the flange 61 to the polyurethane-coated nylon cloth 50. The flange 61 is RF sealed to the inner side of the fourth sheet, on the polyurethane coated portion of the nylon cloth 50.

This flange 61 is preferably formed of Tygon® or polyurethane. Of course, any tube material may be employed which is compatible with the material the device is made from, softens and flows under heating and pressure. The most preferred composition is polyurethane. The flange 61 is formed by cuffing a preformed tube 62 of polyurethane, having a desired diameter and wall thickness, to a predetermined length. A portion of the tube 62, preferably displaced from the ends of the tube 62, is heated and axially compressed in a die 63 having a desired flange shape, and which supports the tube 62 on its inner and outer surfaces at least in the area of heating 64. The wall of the tube 62 in the area of heating 64 is extruded into the die 63, forming a flange 61, with the ends of the tube protruding axially from both sides.

The amount of pressure necessary to deform the walls of the tube 62 into the flange 61 shape depends on the materials, dimensions, heating temperature and heating rate. Using a ¾" urethane tube with a ¹⁄₁₆" wall thickness, approximately 80 lbs of axially applied force is necessary, while a force of 160 lbs significantly shortens the time necessary to form the flange 61.

The flange 61 produced according to the present method does not have any undesirable mold release compound, is stable to the refrigerant compositions, and has no mold partition marks that may induce cracking or failure due to stress and temperature cycling. Thus, while the die 63 must have a parting plane, any surface irregularities formed thereby will be reflected only in the flanged portion, not in the tubular portion. Since the flange 61 does not see particular stresses, and serves mainly to hold the tubular structure in place, the quality of the flange 61 is less important than the quality of the tube 62. The present method creates a high quality tubular structure with a flange portion of equal or better quality than a fully molded part. Further, fabrication defects are reduced because the tube 62 may be inspected prior to flanging, and therefore the incidence of wall defects will be reduced. Further, the normal processes for fabricating polyurethane or Tygon tubes create a tube having superior mechanical properties. These properties are substantially retained in the tubular portions of the present flange 61. A molded flange is normally fabricated of a different composition and does not possess these superior properties and tends to form a weaker tube which is more easily subject to stress failure.

Because the flange 61 is formed through heating in an RF die 63, it is possible to form the flange 61 in situ, i.e. while the formed flange is being sealed to the wall 50 of the bladder 55. This eliminates a fabrication step and reduces the reheating of the flange 61 material. In addition, the flange 61 may be formed with added material in the flanged region 65 by providing a disk of material in the die 63. The flanged tube 62 is therefore RF sealed to the outer polyurethane coated nylon cloth sheet 50 of the cryotherapy device 16, at the outer flange portion thereof. As stated above, the flange 61 may be formed and sealed simultaneously, or formed and then RF sealed to the cryotherapy device 16 in separate steps.

The flanged tube 62 for use as an exhaust valve seat is preferably ¾" O.D. with a ¹⁄₁₆" wall. The resulting flanged tube is approximately 0.6" long, with a flange thickness of approximately ¹⁄₃₂", a protrusion out of the cryotherapy device 16 of about 0.30" and a protrusion into the cryotherapy device 16 of about 0.25". The flange 61 itself has a 1.50" diameter. The flange 61 is located ¼" from one end of the tube 62, but may be moved to the end for certain device configurations.

A flanged tube 62 fabrication method according to the present invention may also be employed to fabricate the inject valve diaphragm 41 from a polyurethane tube.

An exhaust valve 66, for discharging vaporized refrigerant 13, having a pressure relief of 21, 30 or 35 mm Hg is inserted into the flanged tube 62. The exhaust valve 66 has a tubular protrusion 67 from its base 68 with ridges 69, so that it holds firmly in the flanged tube 62, yet can be removed and replaced if desired. The composition of the exhaust valve 66 has a high stiction to the flange material, thereby holding it in place at and above the inflation pressure.

EXAMPLE 7

The discharge or exhaust valve 66 regulates the pressure in the cryotherapy device 16, thereby regulating the pressure that the cryotherapy device 16 exerts on the injury. The exhaust valve 66 also provides a purge function the selectively allows the contents of the bladder 55 to vent to the atmosphere. It is believed that the maximum pressure that can safely be exerted on tissue for any extended length of time is about 40 mm Hg. This number varies with the hydrostatic pressure in the vasculature, but is always close to this range, but may be reduced in poorly vascularized tissues. The maximum time at a pressure above this limit is dependant on tissue temperature, tissue type, injuries or aberrations in the tissue and the like. Therefore, for safety reasons, the pressure is limited to about 35 mm Hg maximum, and for most purposes the refrigerant canister 1 will not last longer than about an hour. Of course, for emergency use, for medically supervised applications, and where otherwise required, larger canisters are available.

Under certain circumstances, it is desirable to block blood flow, especially for limited periods, until medical intervention is available. For example, certain poisons or toxins may or should be contained by the application of peripheral pressure, even at the risk of tissue damage. The application of cold lengthens the time before irreversible damage occurs. Therefore, the present system may find application in the treatment of certain conditions, such as snake or insect bites.

The exhaust valve 56 is preferably a two position valve. In an open condition, the exhaust valve 56 provides a free flow, thereby allowing gas in the cryotherapy device 16 to escape to the environment. This is provided for deflation of the cryotherapy device 16 after use, and to allow shipping where residual refrigerant 13 may produce internal pressure and cause ballooning under certain circumstances, e.g. transport by airplane. The discharge position is preferably one which is unlikely to be accidentally achieved during therapy, such as being activated by pulling or lifting out a portion of the valve. The second position provides a predetermined relief pressure In the cryotherapy device 16, which as stated above is below 35 mm Hg, preferably fixed at one of 21 mm, 30 mm and 35 mm Hg. This exhaust valve 56 should also have a low operating hysteresis, e.g. not have any substantial overpressure for initial activation, so that during initial inflation the cryotherapy device 16 should regulate the pressure accurately and without oscillation or fluctuation. These fluctuations may cause pain, disruption of the injury, and possible secondary trauma, in addition to potentially creating an undesirable tourniquet effect.

The exhaust valve 56 pressure regulating mechanism includes a ball seat 70, a ball 71 and a calibrated spring 72. Below the predetermined pressure, the force of the gas in the cryotherapy device 16 is insufficient to unseat the ball 71 against the predetermined spring 72 pressure, so no venting occurs. When the pressure exceeds the predetermined pressure, the ball 71 becomes unseated from the ball seat 70 and the gas will flow around the ball 71. In normal operation, the ball 71 will be slightly unseated from the ball seat 70 continuously to allow release of the gas which is replaced by the Injected refrigerant 13, without oscillation and probable consequent noise. A steady state is thus achieved. It is noted that a relatively high frequency oscillation will not adversely affect the function of the cryotherapy device 16, save possibly the production of audible noise, and indeed modulated venting is a preferred method of electronically regulating the cryotherapy device 16 pressure. If the pressure in the cryotherapy device 16 falls below the predetermined pressure, the ball 71 will reseat in the ball seat 70, and gas escape will cease, until proper pressure is restored.

Figure 1C:
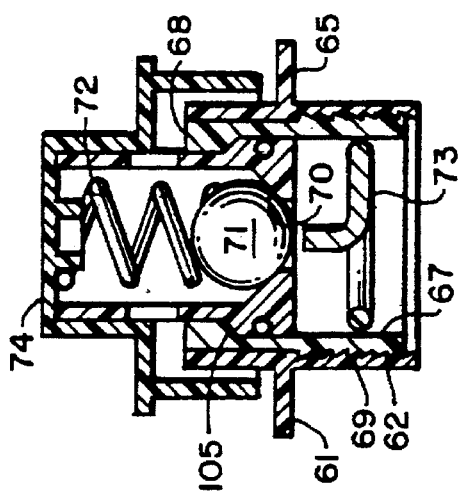
FIGS. 1C and 1D are top and cross sectional views of a pull to inflate exhaust valve.
Figure 1B:
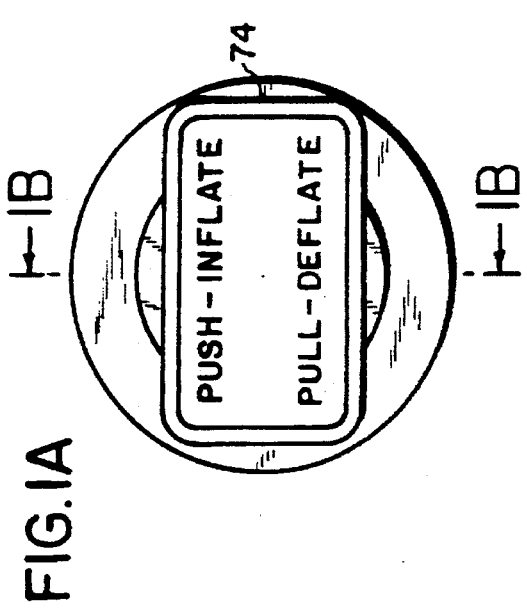
Figure 1D:
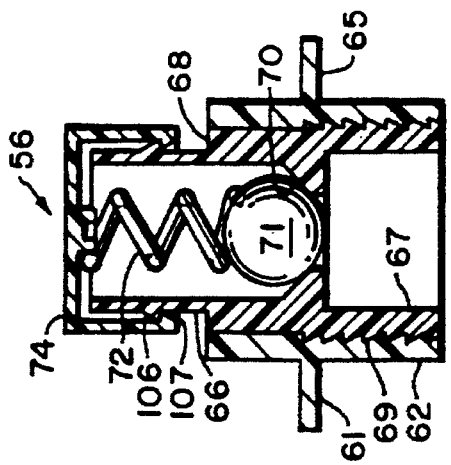
Figure 2A:
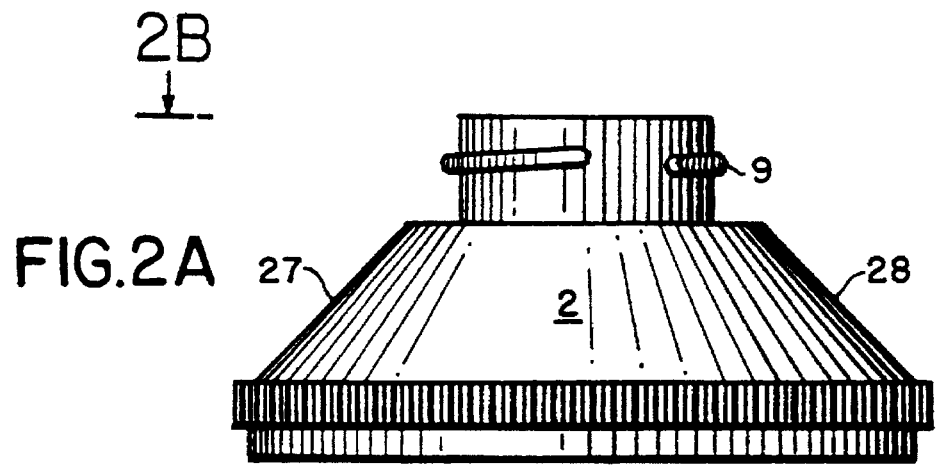
FIG. 2A is a top view of the adapter in accordance with the present invention.
Figure 2B:
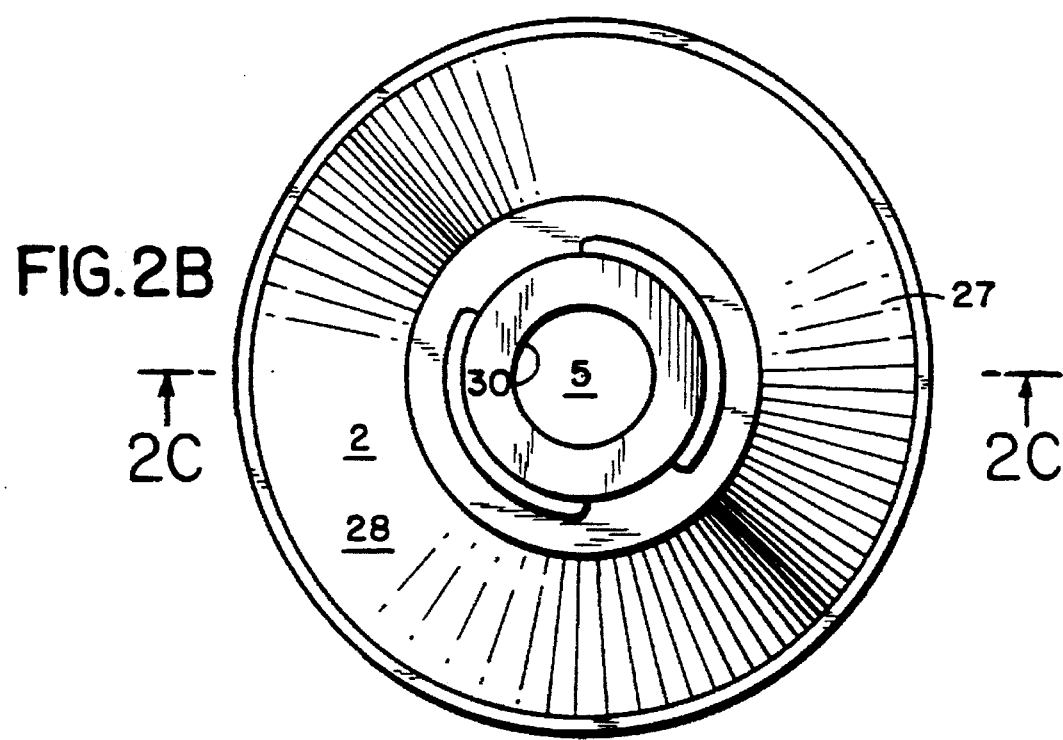
FIG. 2B is a side view of said adapter along line 2B—2B of FIG.2A.
Figure 2C:
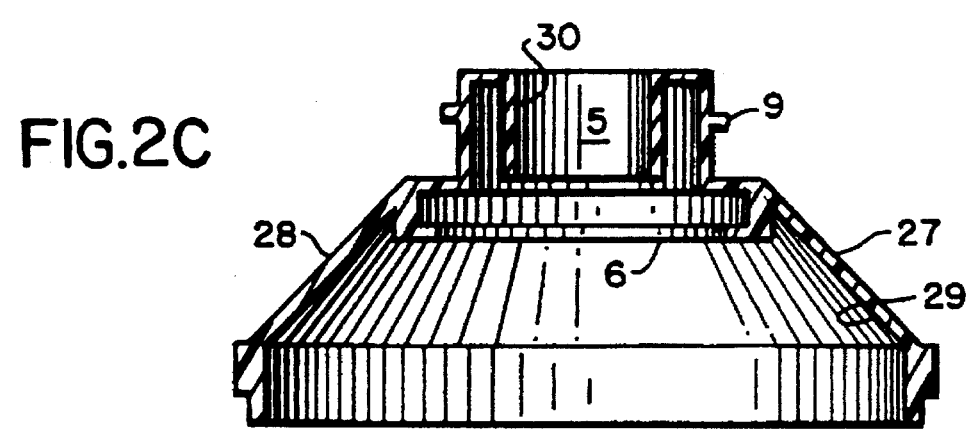
FIG. 2C is a cross-sectional view of said adapter along line 2C—2C of FIG. 2A.
Figure 3A:
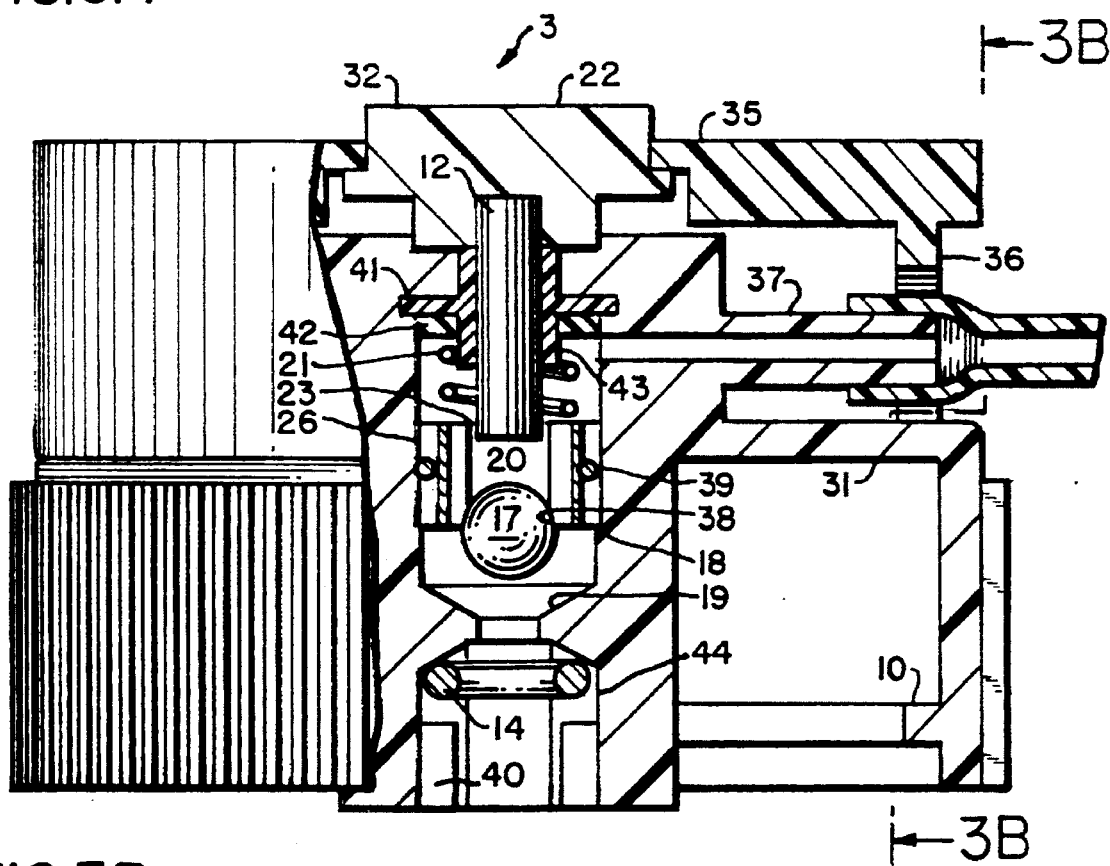
FIG. 3A is a side, partial-section view of an inject valve according to the present invention.
Figure 3B:
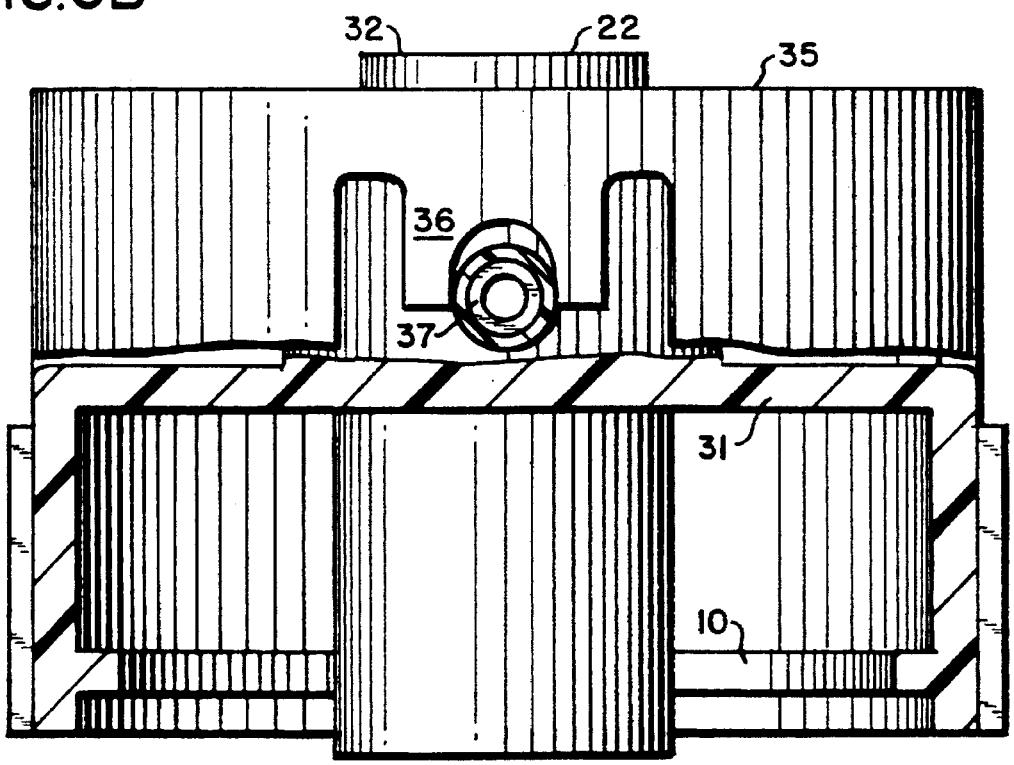
FIG. 3B is an end view of a tube-retaining mechanism shown in FIG. 3A along line 3B—3B.
Figure 4A:
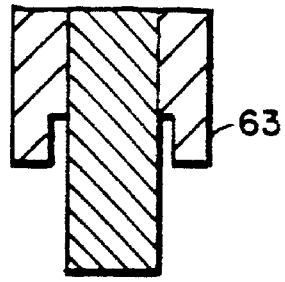
FIGS. 4A and 4B are, respectively, cross-sectional views of a die for making the tube flange and for sealing the flanged valve seat to the side wall of a device, in open and closed configuration.
Figure 4A:
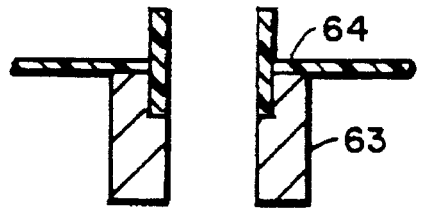
Figure 4B:
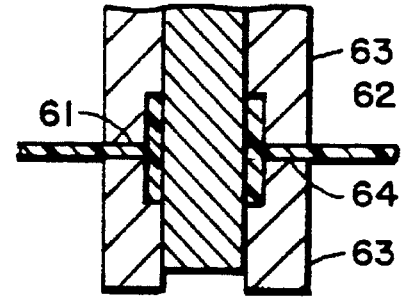
Figure 5A:
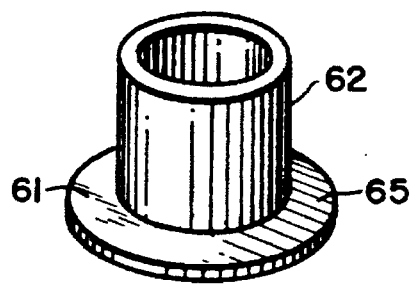
FIG. 5A and 5B are perspective views of flanged tubes in accordance with FIGS. 4A and B respectively.
Figure 5B:
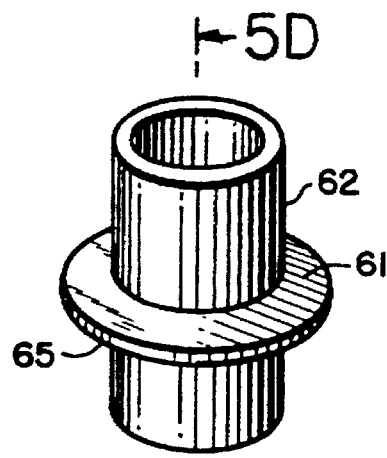
Figure 5C:
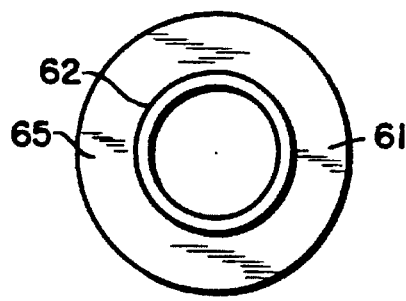
FIG. 5C is a top view of a flanged tube in accordance with the invention.
Figure 5D:
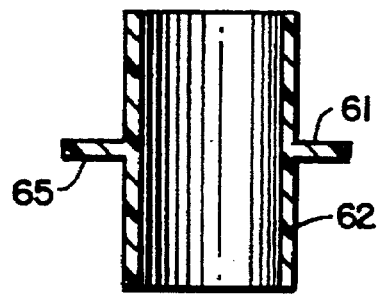
FIG. 5D is a cross-sectional view of the flanged tube of FIG. 5B along line 5D—5D.
Figure 6:
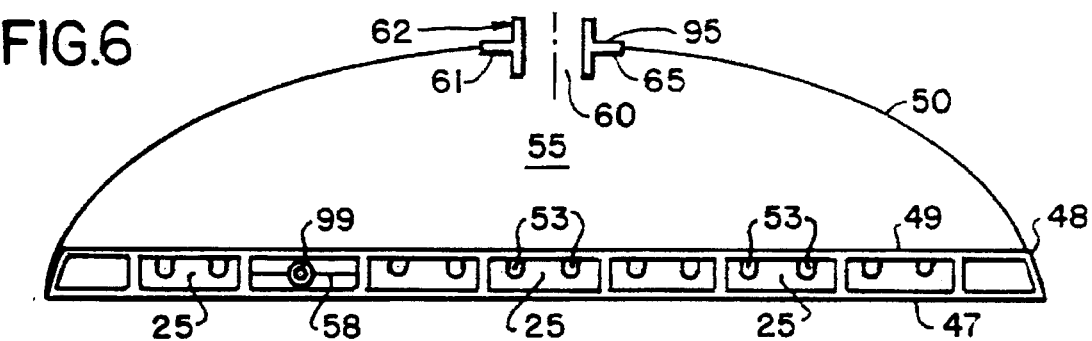
FIG. 6 is a diagrammatic, cross-sectional view of the cryotherapy device according to the present invention.
Figure 8B:
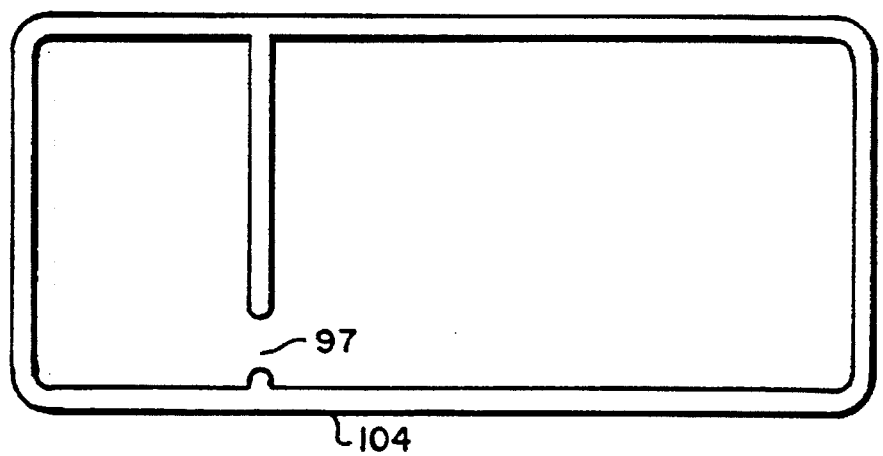
FIG. 8B is a perimeter die for forming the pressure pocket over the maze set forth in FIG. 7.
Figure 8A:
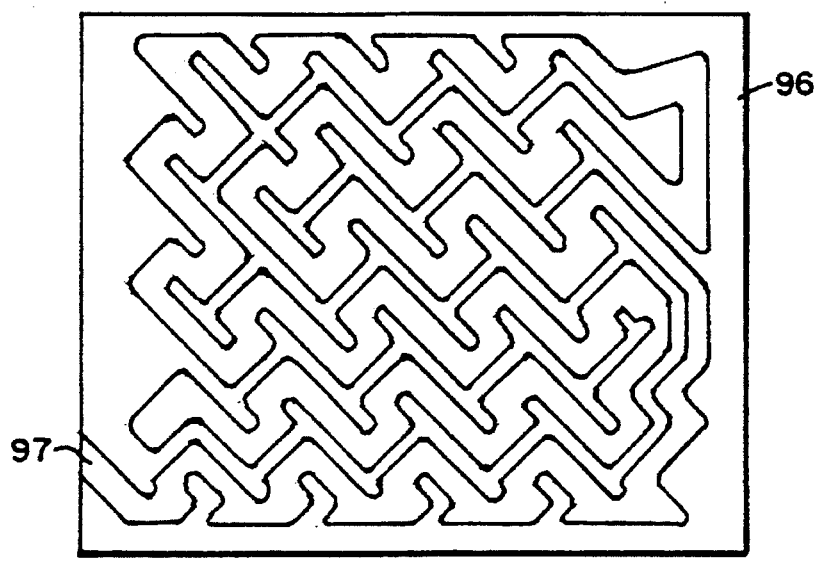
FIG. 8A is a RF-sealing die for forming the maze set forth in FIG 7.
Figure 7:
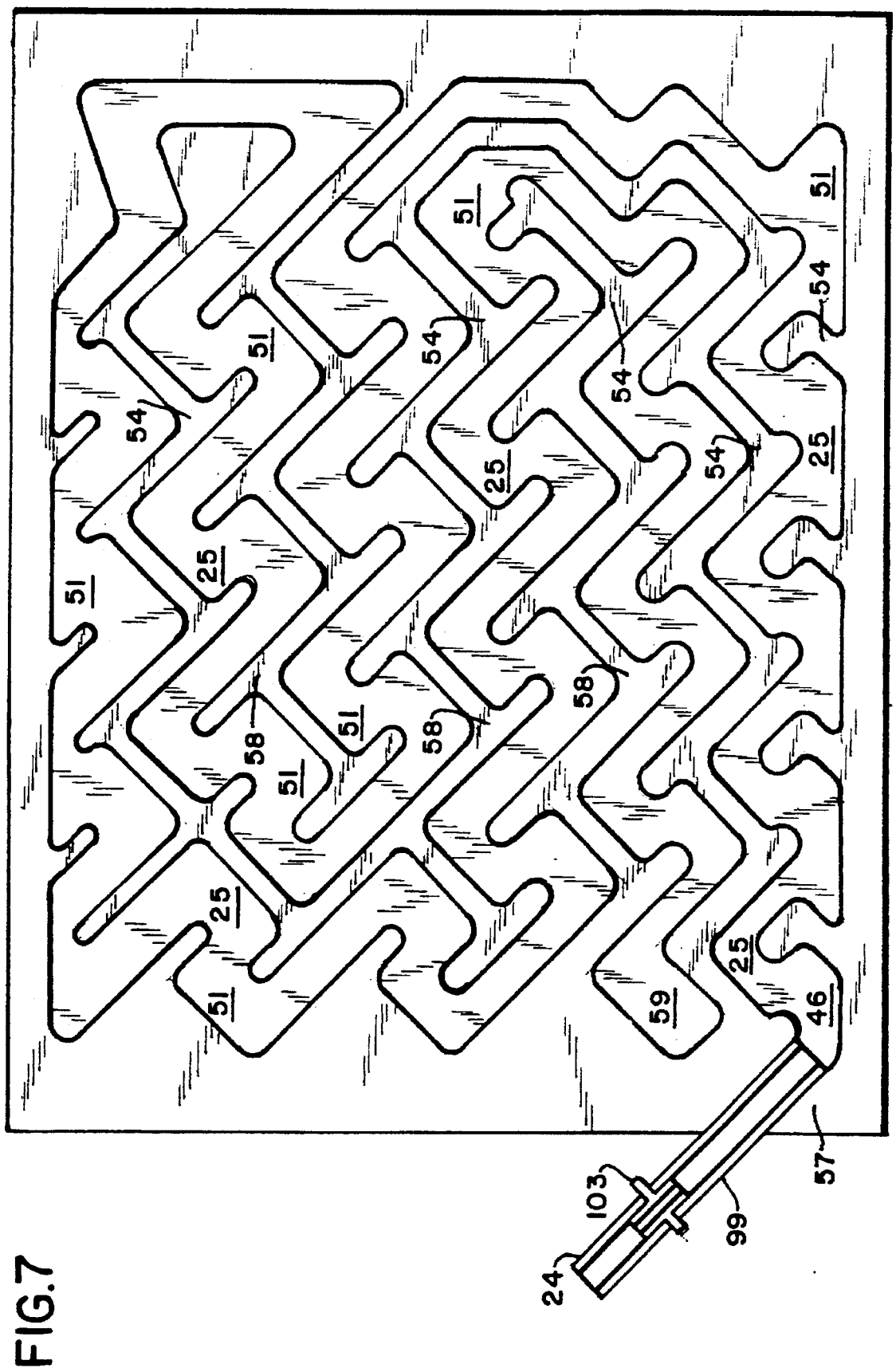
FIG. 7 is a top view of a preferred embodiment of the maze pattern in accordance with the present invention.
Figure 8C:
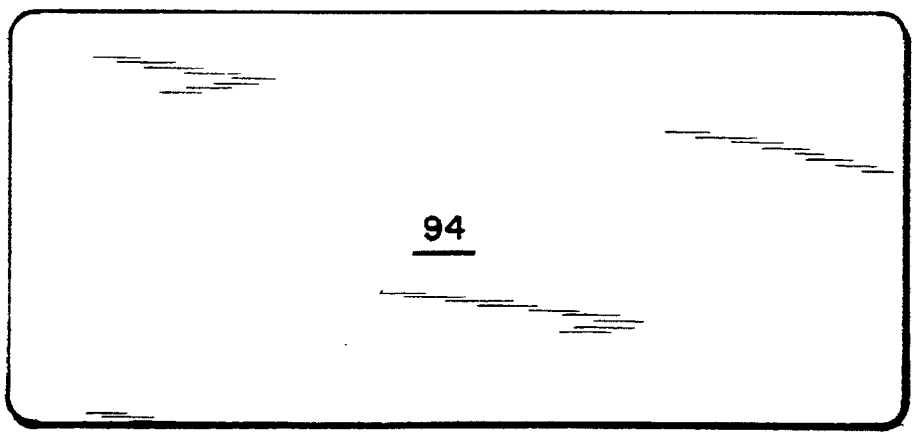
FIG. 8C is die table for forming the maze and pressure pocket of FIGS. 8A and 8B
Figure 9:
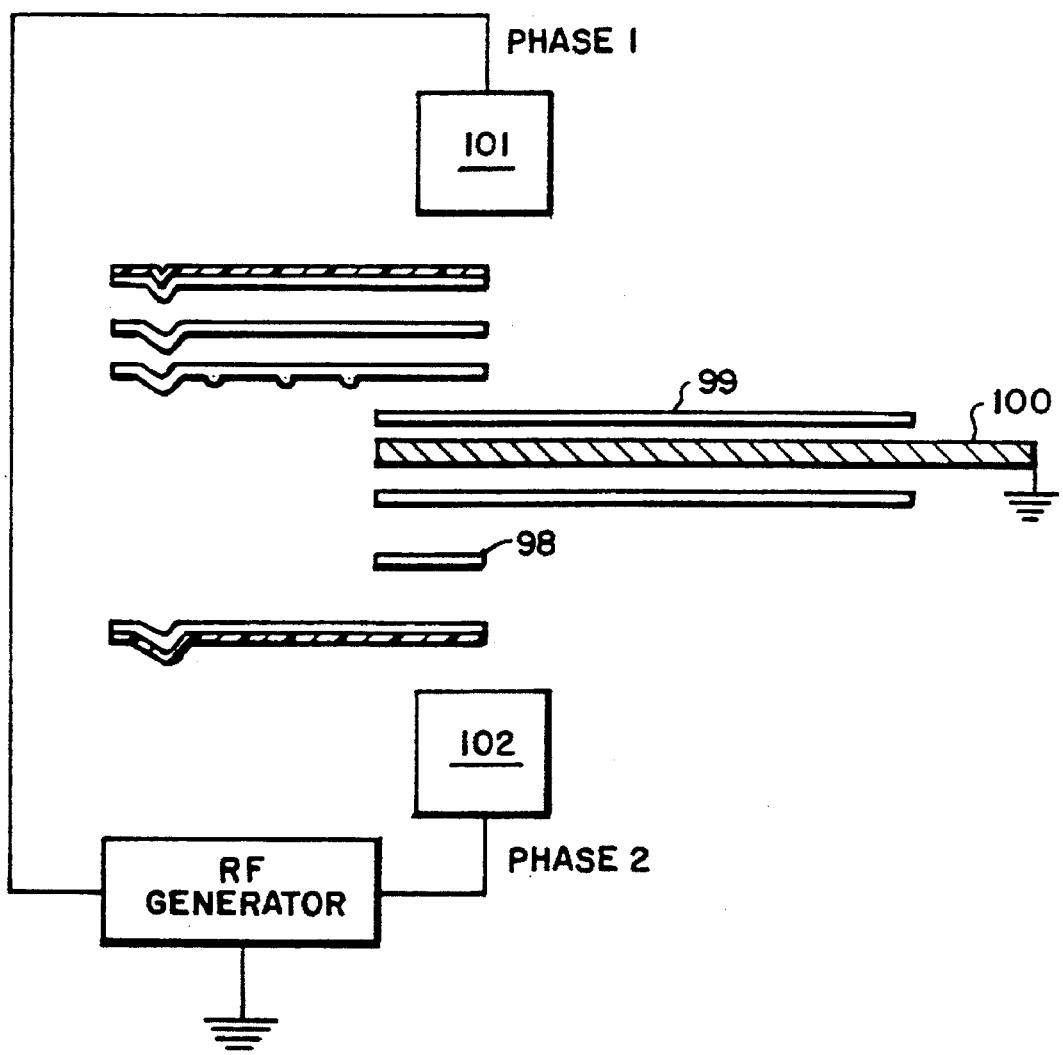
FIG. 9 is a diagrammatic, semi-schematic representation of a dual-sided ceiling technique for the inject location in accordance with the invention.
Figure 10:
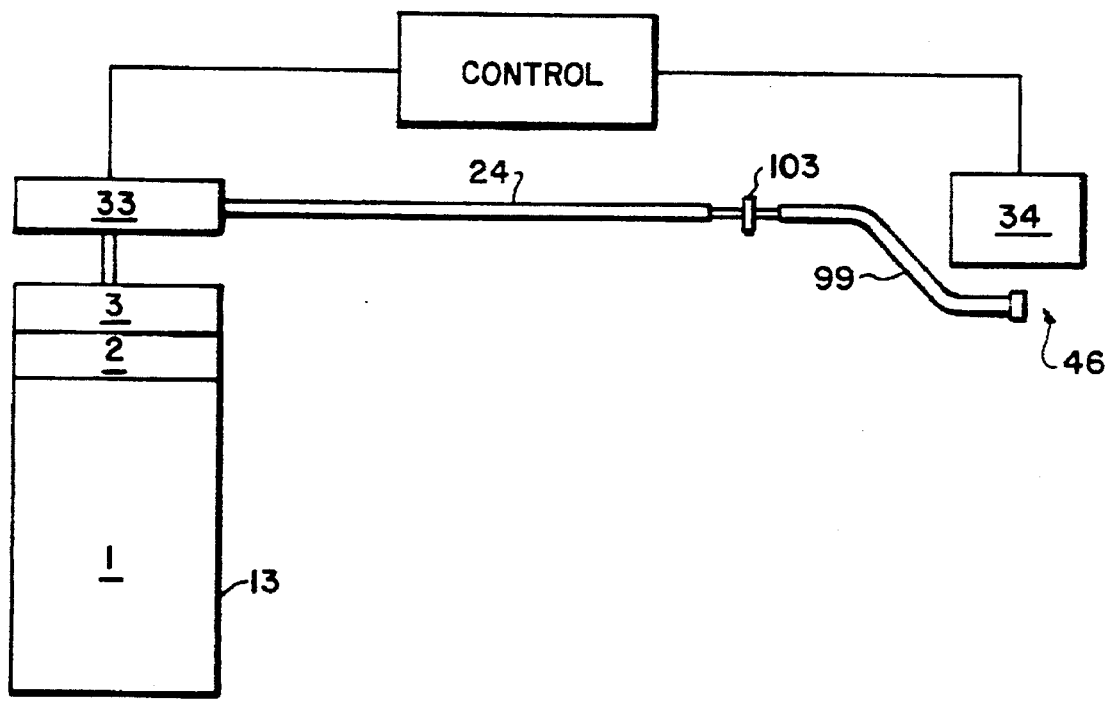
FIG. 10 is a diagrammatic, semi-schematic representation of a temperature feedback control system in accordance with the invention.
Figure 11B:
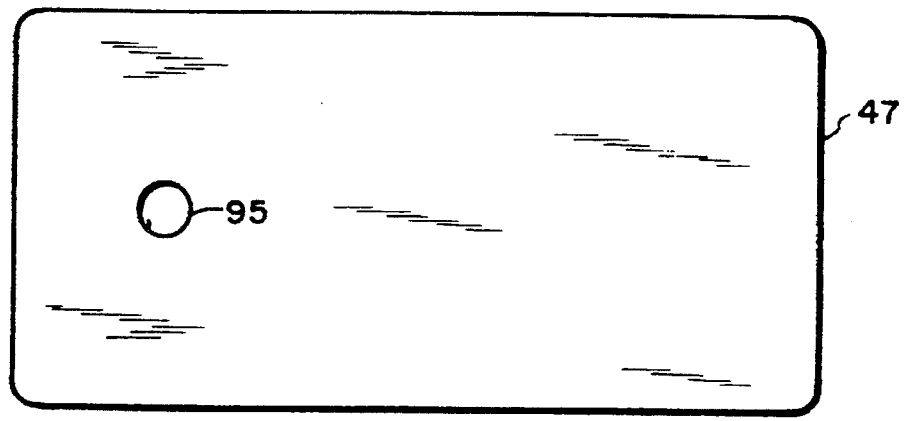
FIG. 11B is a plan view of the center, non-turbulator sheet in accordance with the invention which can be used as a backer sheet for the sheet shown in FIG. 11A.
Figure 11A:
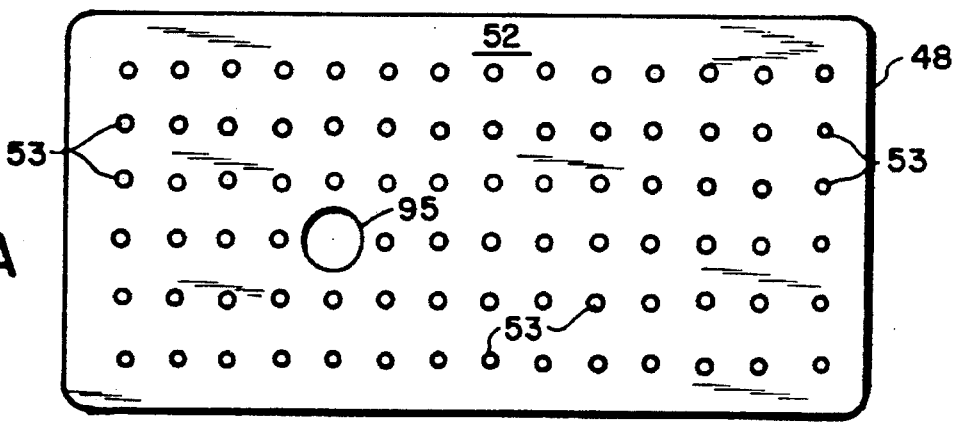
FIG. 11A is a plan view of a sample turbulator sheet in accordance with the invention.
Figure 12:
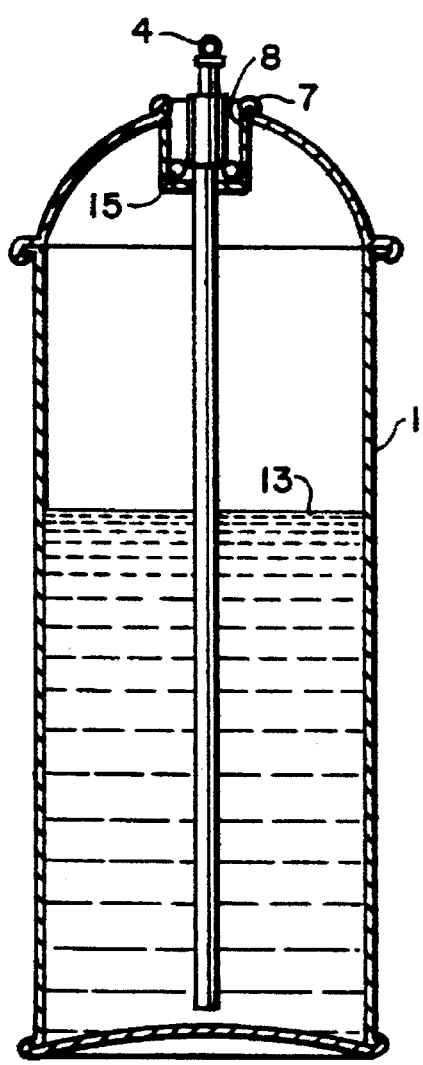
FIG. 12 is a cross-sectional view of a typical canister.
Figure 13A:
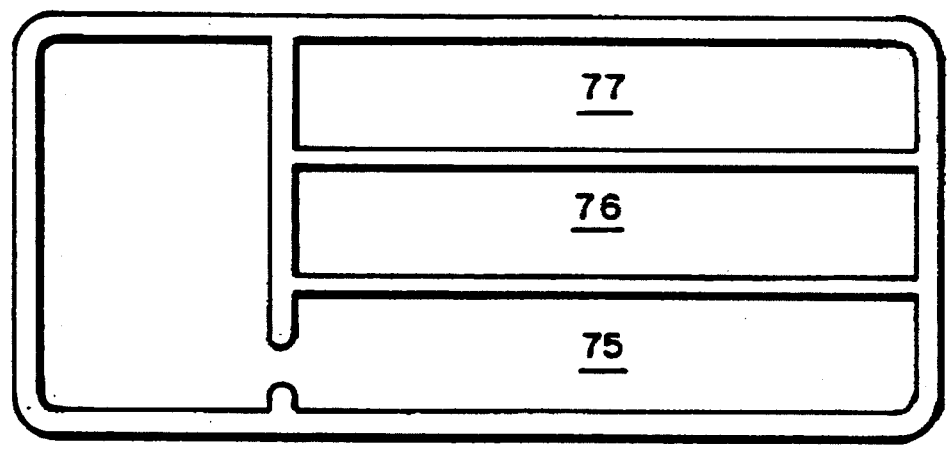
FIG. 13A is a plan view of a perimeter die for a peristaltic pump version for forming the pressure pocket over the maze set forth in FIG. 7.
Figure 13B:
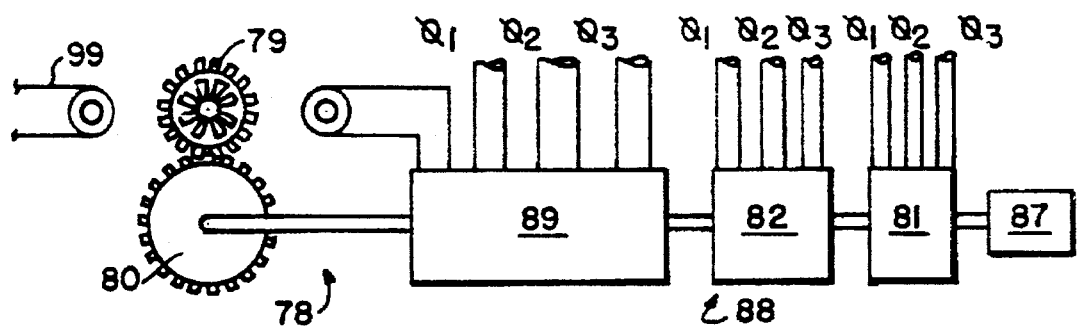
FIG. 13B is a diagrammatic view of a turbine-driven, rotary valve system for a peristaltic pump in accordance with the invention.
Figure 13C:
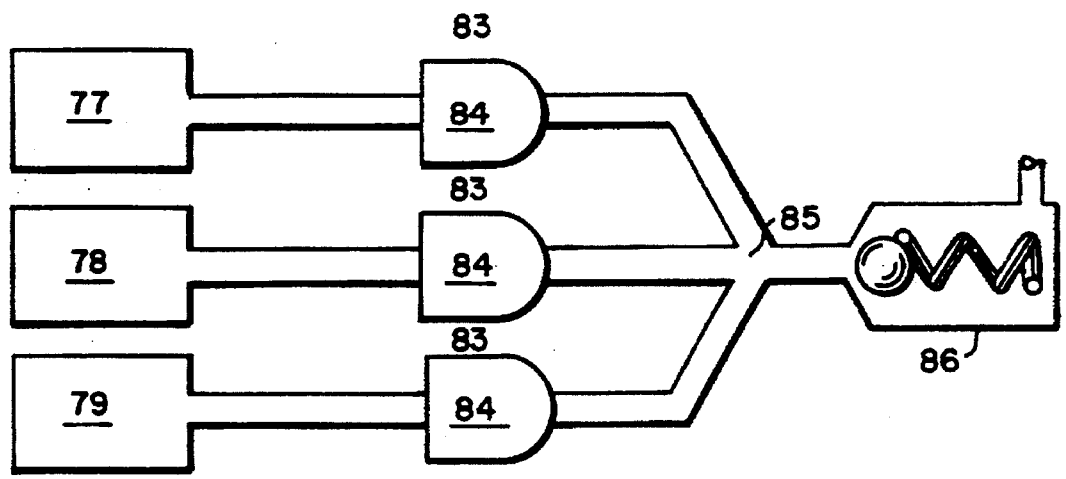
FIG. 13C diagrammatic view of a distribution system for bladders of a peristaltic embodiment emptying through check-valves to a single pressure controlling device.
Figure 14:
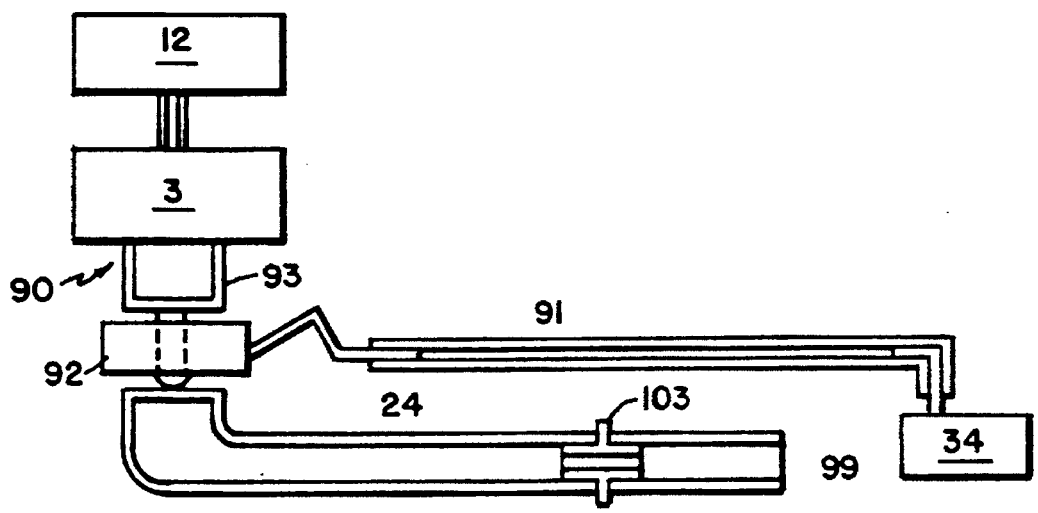
FIG. 14 diagrammatic, semi-schematic view in accordance with a hydraulic feedback, temperature control system of the present invention.

In an preferred embodiment according to the present invention, shown in FIGS. 1A and 1B, the exhaust valve button 74 is linked to the exhaust valve spring 72, so that a lifting of the button 74 causes a reduction in the spring tension, thereby allowing venting to occur. The button 74 is locked in the pressure relief position by a notch 106 which engages a ridge 107 of the button 74. Alternatively, the venting function may be provided by a displacement member 73 which displaces the ball 71 from the valve ball seat 70, thereby allowing the gas to flow unimpeded out of the bladder 55 of the cryotherapy device 16 as shown in FIGS. 1C and 1D. This displacement member 73 is linked to an externally accessible button 74, which is preferably operated by pulling or lifting, In order to avoid accidental deflation. Of course, the venting function may also be engaged by a pushbutton arrangement, with appropriate modifications of the exhaust valve.

EXAMPLE 8

Under certain circumstances, it is preferred that the cryotherapy device 16 be modified to function as a peristaltic pump to assist in tissue circulation. This peristaltic pumping function may also be performed without substantial cooling of the underlying tissue. Thus, a reduction in the amounts of mid and high boiling refrigerants in the mixture, thereby reducing the amount of effective cooling and the heat transfer from the tissue. The peristaltic pumping action may also be accompanied by cryotherapy, where appropriate.

For example, if the cryotherapy device 16 according to the present invention forms a cuff around an arm or leg, with a more distal portion uncovered, then the pressure of the cryotherapy device 16 may cause edema of the distal portion. Further, where long term treatments are indicated or the circulation is fragile, external circulation assistance for venous return may be helpful. In this case, the cryotherapy device 16, formed as a cuff, is divided into at least three pressure bladders, arranged as distal 75, middle 76 and proximal 77 bladders. Of course, a greater number of bladders may be used, up to a number that is limited by practical limitations. A timing mechanism then causes a periodic wave wherein one of the bladders 76 has a reduced pressure, e.g. <15 mm Hg, as compared to the inflated bladders 75, 77 which have a pressure of between about 21 and 35 mm Hg for a few seconds. Of course, with a greater number of bladders, a number of simultaneous peristaltic waves may be present, each having a different phase, but with the same frequency. The sequence of decompression is from distal to proximal, with a continuously repeating cycle. Because of this action, fluid in the tissue, in the veins, lymphatic vessels and interstitial space, is pumped proximally, toward the torso. This system therefore allows the effective treatment of tissue with compromised circulatory drainage.

The timing mechanism may be of any type, but it is preferred that this operate from the flow of refrigerant 13. Therefore, a multi-position discharge valve 78 may be provided in which the flow of refrigerant 13 causes a cycling, sequentially draining and filling the various bladders 75, 76, 77. For this purpose, a simple turbine 79 with a reducing gear 80 may be provided to switch the position of the valve 78. This valve 78 must also ensure that the pressure within any bladder 75, 76, 77 of the cryotherapy device 16 does not exceed 40 mm Hg, and preferable a predetermined pressure between 21 and 35 mm Hg. Thus, it is preferred that a single maze 25 be provided within the cryotherapy device 16 which ensures proper temperature control of the tissue. This maze 25 empties into the bladders 75, 77, with the exception of the discharging bladder 76. Thus, the same valve 78 which discharges the gas from one bladder 76 to the environment may, also in a separate portion prevent flow of refrigerant into that bladder 76. The pressure relief portion 81 of the discharge valve 78 then vents gas as the pressure increases above the predetermined pressure. Prior to discharging a bladder 77, it is preferred that a valve 82 be actuated which equalizes the pressure in the bladder 77 to be discharged with the newly inflating bladder 76, so that the cuff more easily maintains proper pressure without wasted gas. Further, the discharging bladder 77 may have a second regulated pressure, lower than the predetermined pressure, e.g. about 15 mm Hg.

The sequence of the proposed valve 78 for a three bladder system is as follows. Initially, two bladders 75, 77 are inflated to 30 mm Hg, while a third is at 15 mm Hg. All three bladders 75, 76, 77 have check valves 83, which may be a simple flap 84 of sealing material in a conduit 85 to prevent backflow, and are shunted together through a pressure relief discharge valve 86 which exhausts at 30 mm Hg. The bladder 76 inflated to 15 mm Hg is selectively ported to a separate 15 mm Hg pressure relief valve 87, or may bleed to the atmosphere. The gas exiting the maze 25 drives a turbine-wheel 79. A reducing gear 80, driven by the turbine wheel 79 drives a rotary valve body 88 of the discharge valve 78. Because this valve body 88 is internal to the cryotherapy device 16, small amounts of gas leakage around the valve body 88 are not hazardous, and may even be desirable to reduce rotating friction. The gas exiting the turbine 79 enters a separate valve 89, ported to the bladders 75, 77 inflated to 30 mm Hg, but not to the bladder 76 inflated to 15 mm Hg. Therefore, the valve body 88 may be provided with sufficient clearance and configuration to have low friction. When the valve body 88 moves to a new position, It may make a smooth transition or be provided with a snap action detent to minimize intermediate states. As the valve body 88 moves, the flow of gas to the bladder 77 to be emptied ceases, and the gas is ported from the emptying bladder 76 to the bladder 77 which is to be filled, to provide a smooth transition. The 15 mm Hg relief valve 87 connection to the filling bladder 76 is then blocked by a second portion of the valve body 88. Thus, the two bladders 76, 77 which are changing state rapidly equalize to about 22.5 mm Hg. After a short period, the valve body 88 again moves so that the 15 mm Hg relief valve 87 is connected to the deflating bladder 77 and the port of the equalizing valve 82 between the two equalizing bladders 76, 77 is occluded. This sequence is then repeated for each of the possible combinations, to form a peristaltic pump powered by the gas flow.

It is noted that the check valves 83 will have a natural leakage, especially when the gas flow ceases, and therefore a rapid deflation valve is not necessary. If desired, this function may be provided by any of a number of means, including a triple vent valve to vent each bladder without intercommunication when not activated, a mechanical deformation. of the check valve 83 structure to allow leakage, a valve system associated with the rotary valve body which selectively shunts the bladders together and allows venting, and other known systems.

In a preferred embodiment, with three bladders, the entire cycle takes between 30 and 60 seconds for all bladders. The speed will depend on the rate of gas flow, the pressure in the bladders, the characteristics of the tissue to be pumped and the size of the bladders. The peristaltic embodiment is not preferred where continuous pressure should be applied over the entire area of the cryotherapy, where the fluids pooled in the extremity might be contaminated, or where secondary trauma might result as a result of tissue disruption or manipulation. Further, the peristaltic pumping adds complexity to the cryotherapy device 16, and is preferably not be employed where ruggedness and simplicity of operation are necessary. Thus, the peristaltic embodiment is preferable for application a series of medically supervised treatments of injuries or illness which each extend for a long period of time, or are to be applied to en extremity with impaired return circulation.

While the turbine 79 driven valve body 88 is preferred, an electrical or electronic system, employing a motor driven valve or an array of solenoid valves may also be used, especially in conjunction with other electrically powered functionality in the cryotherapy device 16.

The rotating valve body 88 thus has two functions. A first allows gas exiting from the maze 25 to inflate one or two bladders, and the second shunts the remaining bladders together. There is preferably no overlap between the two functions. The inflation phase is preferably about 205 degrees, while the shunting phase is preferably about 145 degrees. The nonoverlap is preferably about 5 degrees. Thus, through about 30 degrees of the cycle ($\frac{1}{12}$ of the total cycle) two bladders are shunted together. Likewise, for about this same period, two bladders are inflated to 30 mm Hg.

The 15 mm Hg pressure relief valve 87 may be controlled using the same rotating valve body 88 as controls inflation of the bladders 75, 76, 77. This function is preferably provided through a separate flow path. A fluidic valve control system may also be employed. In addition, a gas flow control system based on pressure accumulation and volume redistribution may also be constructed.

While the above description describes a three bladder system, a system having more than three bladders may also be constructed according to the same principles. A two bladder system may also be constructed, which, though generally less effective as a peristaltic pump, intermittently relieves pressure in the underlying tissue, and allows a simplified control system.

EXAMPLE 9

The control system for the device according to the present invention may include a thermostat as the temperature sensor 34, for controlling the temperature of the tissue. The temperature should preferably be measured at the inject port 46 of the maze 25, which will most likely be the lowest temperature portion. This temperature is regulated so that it remains above 36 F., so that the risk of tissue freezing or frostbite is minimized. The temperature sensor 34 may include a bimetallic element, an expandable fluid, an electronic thermometer or other known temperature sensing device.

A bimetallic element is preferred for its simplicity and because the mechanical motion created by the temperature change can be transmitted directly to control the refrigerant 13 flow. In this case, a secondary valve 90 is formed near the inject port 46 of the maze 25, which is proportionally or thermostatically controlled. This secondary valve 90 slows or stops the refrigerant 13 flow into the maze 25 if the temperature drops too low, and likewise increases the flow if the temperature rises. It is noted however, that with a secondary valve 90 at in the cryotherapy device 16, the pressure In the umbilical tube 24 may be increased to high levels. Therefore, the attachment system must accommodate such pressures without risk of failure.

Alternatively, the bimetallic element may exert a pressure on a fluid (e.g. alcohol, antifreeze, e.g. polyethylene glycol solution or mineral oil), which force is transmitted from the cryotherapy device 16 to the inject valve 3 through a second tube 91, which runs parallel to the umbilical refrigerant tube 24. The fluid in the second tube 91, in. turn, controls a flow rate of the refrigerant 13 in the inject valve 3, positively related to the temperature. Thus, if the temperature in the cryotherapy device 16 is too low, the flow rate is decreased, and likewise, If the temperature is too high the flow rate is increased. This regulation may be proportional or thermostatic. The minimum flow rate is preferably established by a bypass aperture, so that some refrigerant always flows, in order to avoid deflation of the bladder 55 and to provide a failsafe mechanism in case of failure of the temperature regulating mechanism. The maximum flow rate is preferably limited to a predetermined safe rate. The pressure in the second tube 91 may control the flow rate by moving an occluding member 92 in relation to a refrigerant flow aperture 93, applying a compensating force to a pressure relief valve, or other known methods. In the present system employing narrow bypass orifices 26, a cross member may be used as the occluding member 92, which may be displaced according to the temperature to interrupt a flow through one or more orifices 26, thereby modulating refrigerant 13 flow.

In another embodiment, a temperature sensor in the cryotherapy device 16 may produce a detectable pressure pulsation which is transmitted in retrograde fashion up the tube 24. This pulsation, when detected, may be deciphered as a temperature control signal. Thus, if the temperature drops too low, a thermostat may allow a member to vibrate from the flow of refrigerant, while when the temperature is too high, the member is outside the flow path and therefore does not vibrate. In the inject valve, a vibration sensor tuned to the vibrational frequency of the thermostatic controlled member near the inject port 46 monitors the refrigerant tube 24. When no vibration is detected, a normal flow of refrigerant is allowed. When vibration is detected, the vibration sensor variably occludes an orifice for the refrigerant flow. Therefore, when the temperature drops too low, a thermostatic sensor detects the condition and causes the member to vibrate. The vibration is transmitted up the refrigerant flow tube and is detected by a vibration sensor, which reduces the flow rate during the period of vibration.

An electronic thermometer may also be provided as the temperature sensor 34, which detects a temperature near the inject port 46 ion of the maze 25. The electronic thermometer is a device which employs a sensor having an electrical output corresponding to temperature. An electrical thermostat, preset to detect conditions above or below 36 F. may also be used. The electrical output signal may then be displayed as an analog or numeric display, or be employed as an input to an electronic control device for regulating a characteristic of the operation of the cryotherapy device 16, such as temperature or time of treatment. In such a control system, the electrical output signal is preferably transmitted by means of a pair of wires to the inject valve 3, which regulates the refrigerant 13 flow by means of an electrically operated valve. The valve may be of any suitable known type, although a preferred type is a piezoelectric valve. A piezoelectric valve may operate to selectively occlude a narrow orifice 26 by applying a voltage to a piezoelectric material. The applied voltage causes a change in a dimension of the piezoelectric material, thereby allowing a mechanical control function. These piezoelectric materials may be stacked to increase a resulting amount of movement. The piezoelectric material may therefore be used to block or allow flow through the small bypass aperture. While a high voltage is generally necessary for operation of these devices, they generally require low power so they may be battery operated. Alternatively, a solenoid valve may be used to modulate refrigerant 13 flow through the orifice 26.

An electronic thermometer embodiment is preferred, however, where a very large area with widely varying characteristics is to be coveted. For example, in a full leg cryotherapy device or full upper body cryotherapy device, the tissue heat production may vary widely, along with the local environmental conditions (e.g., exposed to air or resting on a bed). In this case, multiple thermostatically or thermometrically (e.g. binary or proportional) controlled inject valves with multiple maze flow paths provide the advantage of a tighter degree of control over local temperature, and lower spatial variation, over the entire area to be treated. In this case, the inject valve system includes a plurality of orifices, each controlled by a separate electronic valve and a separate temperature sensor, and each orifice feeding a separate umbilical tube 24 to the cryotherapy device 16. Alternatively, a single high pressure tube may feed the entire heat transfer portion of the cryotherapy device 16, which contains the control system internally, thereby minimizing the necessary external cabling and tubing. It is noted that the temperature sensors need not correspond in a one-to-one fashion to the valve actuators, and an electronic control may integrate a sensor array and control the actuators as an interrelated system. Therefore, the number of temperature sensors may be less than or greater than the number of valve actuators. In such a case it is preferred that a control include a model-based or fuzzy logic control, possibly with adaptive characteristics. This control may be implemented in a standard 8-bit microprocessor, such as a Motorola 68HC11 or 80C51 derivative.

EXAMPLE 10

The cryotherapy device 16 may be formed as follows. A piece of polyurethane coated nylon cloth sheet 49 is placed polyurethane side up on a die table 94. A textured polyurethane sheet 48, having surface features 53, which are protrusions, ribs, an interrupted spline, or other texturing. The sheet 48 is placed texturing down on top of the inlet tube 24, with a smooth polyurethane sheet 47 placed on top of the textured sheet 48. The two polyurethane sheets 47, 48 have aligned holes 95, providing a vent from the maze 25. An RF heating die 96 then is placed over the aligned sheets 47, 48, with care to align a notch 97 in the die 96 with the location for the inlet tube 24, and the die 96 is heated and pressed against the die table 94, causing fusion of the polyurethane in the pattern of the die 96 and sealing of the inlet tube 24 to fix it in place and prevent leakage. These steps can, of course, be performed separately and need not be done simultaneously.

The inlet tube 24 may be sealed directly to the maze 25 in an initial formation process. The inlet tube 24 is positioned in place, leading from an edge of the sheets 47, 48, 49, with a plastic sealing band 98 made of polyurethane placed under the tube 24 in the direction of the tube 24. Preferably, however, the tube 24 is added in a separate later operation. A short length of tube 99, with a ground rod 100 inserted therein, is placed in the opening for the tube 99 in the cryotherapy device 16. The polyurethane plastic sealing band 98 is placed next to the tube 99 to provide added material for fusion and sealing. A first RF sealing operation with a first sealing die 101 seals the maze material to the tube 99 from one side, followed immediately by a second RF sealing operation with a second RF sealing die 102 from the opposite side. Both RF sealing operations use the ground rod 100 in the tube 99. The ground rod 100 is then removed and a tube connector 103 affixed to the short length of tube 99, to attach the umbilical tube 24.

A dimpling may be provided as the surface features 53 on an inner surface of the maze 25, which helps to create turbulence, maintain the patency of the maze 25 lumen, and increase the surface area of the maze 25. The dimpled surface allows a construction in which the polyurethane-coated sheets need not be particularly aligned prior to the RF sealing steps. Ribs, splines, and other types of texturing which are specially aligned with the maze 25 may provide slightly improved characteristics, but are more difficult to fabricate.

After the maze 25 is fabricated, a second sheet of polyurethane coated nylon cloth 50 is then placed, polyurethane side down over the maze 25 structure, and sealed about its periphery to the three other sheets 49, 48, 47 by means of an RF heated die 104 and pressure. This second sheet of polyurethane coated cloth 50 has a discharge valve seat 60, which is formed by a flange 61, formed of a polyurethane or Tygon® tube 24 RF sealed to it in an appropriate location.

EXAMPLE 11

A refrigerant mixture is produced by mixing, by weight 40% 152A (low boiling), 20% 142B (mid boiling) and 40% 123 (high boiling). 8 ounces of this mixture is placed in a 6½ inch aerosol canister 1, having a compatible sealing material system.

The refrigerant mixture may also include 124 instead of 142B. The proportions may also be one third each of the components by weight. The proportions may also be 20% 152A, 40% 142B and 40% 123.

Aerosol canisters having carbon dioxide filled bladders to propel the contents are available. If such an arrangement is employed, a mixture having around 20% or less of the lowest boiling component may be employed, while still ensuring flow of liquid refrigerant 13 from the canister 1.

It should be understood that the preferred embodiments and examples described herein are for illustrative purposes only and are not to be construed as limiting the scope of the present invention, which is properly delineated only in the appended claims.

We claim:

1. A cryotherapy apparatus comprising:

a refrigerant canister having an integral valve with a valve stem and a lip;

an adapter, mating with said refrigerant canister at said lip, having an aperture into which said valve stem protrudes;

an inject valve, adapted for mounting on and dismounting from said adapter, and activating said integral valve when mounted on said adapter, a selectively activated passage having a high flow rate and flow-restricted passage allowing a low flow rate;

a tube, mounted to said inject valve by a nipple inserted into said tube and locked by an external constrictor around said tube and said nipple;

a maze, having a passage formed between two sheets sealed into a pattern having a plurality of blind ends in a plurality of orientations, said maze having at least one wall having a textured surface and receiving said tube at one end, and having an apparent cross-sectional area which increases with increasing distance from said tube;

an expansion space, formed by a layer of material on one side of said maze, being parallel to said maze, into which an end of said maze distal from said tube empties;

a flange, formed in a wall of said expansion space opposite said maze; and a pressure regulating discharge valve having a pressure regulating function and a selectively activated gas discharging function, mounted at said flange.

2. The applicator according to claim 1, wherein the inject valve mounts to said adapter by means comprising a pair of mating mutually rotating inclined sliding wedges.

3. The cryotherapy system according to claim 1, further comprising a thermal sensor associated with said canister for determining an amount of refrigerant remaining.

4. A cryotherapy applicator comprising:

a maze, having a passage formed between two sheets sealed into a pattern having a plurality ends in a plurality of orientations, said maze having at least one wall having a textured surface, said passage having a tube at one end, and having an apparent cross sectional area which increases with increasing distance from said tube;

an expansion space, formed by a layer of material on one side of said maze, being parallel to said maze, into which an end of said maze distal from said tube empties; and a restricted flow exhaust from said expansion space to the atmosphere for maintain a superatmospheric pressure in said expansion space under conditions of flow through said maze.

5. The applicator according to claim 4, further comprising an inject having a restricted flow aperture and a selectively operable bypass path, wherein a cross sectional area of the bypass path is greater than a cross sectional area of the restricted flow aperture, said inject valve being disposed in series with said tube.

6. The applicator according to claim 5, wherein said bypass path comprises a ball, a first ball seat and a second ball seat, wherein said ball is displaceable from said first ball seat to allow a flow therethrough, under positive flow conditions, and said ball is urged toward said second ball seat to form a check valve under negative flow conditions, said first ball seat bypassing said restricted flow aperture and said second ball seat sealing leakage through said restricted flow aperture.

7. The applicator according to claim 4, wherein one of the sheets forming said maze has surface features for creating turbulence in flowing refrigerant liquid.

8. The applicator according to claim 7, wherein said surface features are selected from the group consisting of bumps, protrusions, projections into the maze lumen, and an interrupted spline.

9. The applicator according to claim 4, wherein said restricted flow exhaust comprises a pressure relief valve.

10. The applicator according to claim 9, wherein said pressure relief valve has a fixed relief pressure.

11. The applicator according to claim 10, wherein said pressure relief valve has a relief pressure of between 15–40 mm Hg.

12. The applicator according to claim 11, wherein said relief pressure is about 21 mm Hg.

13. The applicator according to claim 10, wherein said pressure relief valve comprises a selectively activated venting port to empty the expansion space.

14. The applicator according to claim 4, wherein said walls of said maze comprise polyurethane.

15. The applicator according to claim 4, wherein said applicator is adapted to conform to an anatomical area selected from the group consisting of the human head, forehead, face, neck, shoulder, full arm, forearm, elbow, wrist, hip, hand, shoulder and chest, chest and upper back, lower back, full leg, thigh, knee, patella, calf, ankle and foot.

16. The applicator according to claim 4, wherein said maze is adapted to conform to an anatomical area selected from the group consisting of the equine full leg, ankle, hock and cannon bone.

17. The applicator according to claim 4 further comprising a pressure transducer and a electronic control for controlling said superatmospheric pressure in said expansion space.

18. The applicator according to claim 4, further comprising a temperature transducer and a control for controlling a temperature of said maze.

19. The applicator according to claim 4, wherein said maze is adapted to treat an anatomical area having an axis, wherein the maze comprises a path generally oriented at 45 degrees from said axis of said anatomical area.

20. The applicator according to claim 4, wherein said expansion space comprises a plurality of chambers, further comprising a control system for pressurizing and depressurizing said plurality of chambers rhythmically to form a peristaltic pump for fluids in the tissue under treatment.

21. The applicator according to claim 4, wherein one sheet of said maze comprises polyurethane coated nylon cloth.

22. The apparatus according to claim 4, wherein said layer of material of said expansion space comprises polyurethane coated nylon cloth.

* * * * *